US006391940B1

United States Patent
Blackwell et al.

(10) Patent No.: US 6,391,940 B1
(45) Date of Patent: May 21, 2002

(54) METHOD AND COMPOSITION FOR ADHERING TO METAL DENTAL STRUCTURE

(75) Inventors: Gordon Brian Blackwell, Constance (DE); Kewang Lu, Dover, DE (US); Chin-Teh Huang, Wufeng (TW); Mingxin Fan, West Chester, PA (US); Paul D. Hammesfahr, Wyoming, DE (US); Xiuling Wang; Junjie Sang, both of Magnolia, DE (US)

(73) Assignee: Dentsply Research & Development Corp.

( * ) Notice: Subject to any disclaimer, the term of this patent is extended or adjusted under 35 U.S.C. 154(b) by 0 days.

(21) Appl. No.: 09/342,825

(22) Filed: Jun. 29, 1999

Related U.S. Application Data

(63) Continuation of application No. 09/290,962, filed on Apr. 13, 1999, now Pat. No. 6,191,190, which is a continuation-in-part of application No. 09/080,781, filed on May 18, 1998, which is a continuation-in-part of application No. 08/627,339, filed on Apr. 4, 1996, now Pat. No. 5,756,559, which is a continuation of application No. 08/292,104, filed on Aug. 22, 1994, now abandoned, which is a continuation-in-part of application No. 09/093,548, filed on Jun. 8, 1998, now abandoned, which is a continuation of application No. 08/995,997, filed on Dec. 22, 1997, now Pat. No. 5,955,514, which is a continuation of application No. 08/259,833, filed on Jun. 15, 1994, which is a continuation-in-part of application No. 08/049,221, filed on Apr. 19, 1993, now Pat. No. 5,338,773.

(51) Int. Cl.⁷ .............................. C08K 5/49; A61F 2/00; C08F 18/16

(52) U.S. Cl. ................... 523/115; 523/118; 524/116; 524/117; 524/118; 524/356; 524/770; 526/318.1; 526/326

(58) Field of Search ..................... 523/115, 118; 524/116, 117, 118, 356, 770; 526/318.1, 326

(56) References Cited

U.S. PATENT DOCUMENTS

| | | | |
|---|---|---|---|
| 2,549,732 A | 4/1951 | Weaver | 260/40 |
| 2,568,331 A | 9/1951 | Frilette | 260/40 |
| 2,628,209 A | 10/1953 | Fisk | 260/40 |
| 2,673,151 A | 3/1954 | Gerhart | 95/7 |
| 2,929,143 A | 3/1960 | Roubian | 32/1 |
| 3,013,895 A | 12/1961 | Agruss | 117/38 |
| 3,234,181 A | 2/1966 | Olivier | 260/47 |
| 3,309,772 A | 3/1967 | Lieb et al. | 32/48 |
| 3,407,176 A | 10/1968 | Loncrini | 260/47 |
| 3,421,501 A | 1/1969 | Beightol | 128/90 |
| 3,422,061 A | 1/1969 | Gall | 260/47 |
| 3,424,718 A | 1/1969 | Angelo | 260/47 |
| 3,448,089 A | 6/1969 | Celeste | 260/78.5 |
| 3,518,762 A | 7/1970 | Takeuchi | 32/13 |
| 3,655,605 A | 4/1972 | Smith | 260/29.6 |
| 3,785,832 A | 1/1974 | Bowen | 106/35 |
| 3,789,462 A | 2/1974 | Reich | 32/59 |
| 3,814,717 A | 6/1974 | Wilson et al. | 260/29.6 |
| 3,855,379 A | 12/1974 | Araki et al. | 260/77.5 |
| 3,884,886 A | 5/1975 | Pluddemann | 260/89 |
| 3,954,475 A | 5/1976 | Abonham et al. | 96/67 |
| 3,959,350 A | 5/1976 | Rogers | 260/47 |
| 4,001,939 A | 1/1977 | Gross | 32/15 |
| 4,012,840 A | 3/1977 | Takeuchi et al. | 32/15 |
| 4,016,124 A | 4/1977 | Crisp et al. | 260/29.6 |
| 4,021,915 A | 5/1977 | Rubens | 32/15 |
| 4,035,321 A | 7/1977 | Shahidi et al. | 260/22 |
| 4,043,327 A | 8/1977 | Potter et al. | 128/89 |
| 4,048,765 A | 9/1977 | Samuelson | 51/328 |
| 4,055,897 A | 11/1977 | Brix | 32/59 |
| 4,064,629 A | 12/1977 | Stoner et al. | 32/15 |

(List continued on next page.)

FOREIGN PATENT DOCUMENTS

| | | |
|---|---|---|
| AU | 46717/89 | 6/1990 |
| CA | 873935 | 6/1971 |
| CA | 934085 | 9/1973 |

(List continued on next page.)

OTHER PUBLICATIONS

McKinney et al, Wear and Microhardening of Two Experimental Dental Composites, Journal of Dental Research, vol. 65, p. 848, Abstract No. 1101 (1986).

Antonucci et al, Formulation and Evaluation of Resin–Modified Glass Ionomer Cements, Transactions Thirteenth Annual Meeting of the Society for Biomaterials, Jun. 3–7, 1987, vol. X.

Antonucci, Toughened Glass Ionomer Cements, Trends & Techniques, Apr. 1988, vol. 5, No. 3.

(List continued on next page.)

*Primary Examiner*—Kriellion A. Sanders
(74) *Attorney, Agent, or Firm*—Dale R. Lovercheck; James B. Bieber

(57) ABSTRACT

A preferred embodiment of the invention provides a composition and method of treating dental metal. The composition includes a polymerizable aryl compound having at least one carboxylic acid group and at least one polymerizable group, and a polymerizable compound having at least one polymerizable group and at least one phosphorous containing group. A preferred composition includes at least 50 percent by weight of a volatile organic solvent, at least 15 percent by weight of one or more polymerizable acrylate compounds and an effective amount of a photoinitiator. At least a portion of the polymerizable compounds are multifunctional polymerizable compounds having at least three acrylate moieties. The polymerizable compounds are substantially soluble in the solvent. The composition is adapted to form a polymeric material which is adapted to adhere to metal and ceramics and to dentin. Compositions of the invention have superior adhesion to dental metals and tooth without separately acid etching dentin or enamel. Compositions are useful as dental priming adhesives, luting cements, liners, pit and fissure sealants, bases and restoratives.

80 Claims, No Drawings

U.S. PATENT DOCUMENTS

| | | | |
|---|---|---|---|
| 4,089,830 A | 5/1978 | Tezu | 260/29.6 |
| 4,107,845 A | 8/1978 | Lee, Jr. et al. | 32/15 |
| 4,143,018 A | 3/1979 | Crsip et al. | 260/29.6 |
| 4,180,911 A | 1/1980 | Bullock | 433/9 |
| 4,182,035 A | 1/1980 | Yamauchi et al. | 433/228 |
| 4,209,434 A | 6/1980 | Wilson et al. | 260/29.6 |
| 4,212,970 A | 7/1980 | Iwasaki | 542/455 |
| 4,243,567 A | 1/1981 | Potter | 260/29.6 |
| 4,317,681 A | 3/1982 | Beede et al. | 106/85 |
| 4,322,207 A | 3/1982 | Madsen | 433/216 |
| 4,324,591 A | 4/1982 | Beede et al. | 106/85 |
| 4,338,748 A | 7/1982 | Elbel | 51/206 |
| 4,342,677 A | 8/1982 | Muramatsu | 523/116 |
| 4,358,549 A | 11/1982 | Randklev | 523/117 |
| 4,360,605 A | 11/1982 | Schmitt et al. | 523/116 |
| 4,366,175 A | 12/1982 | Gibbs | 524/726 |
| 4,372,836 A | 2/1983 | Schmitt et al. | 523/159.23 |
| 4,374,936 A | 2/1983 | Tomioka et al. | 523/116 |
| 4,376,835 A | 3/1983 | Schmitt et al. | 523/116 |
| 4,378,213 A | 3/1983 | Severy | 433/213 |
| 4,401,773 A | 8/1983 | Smyth | 523/106 |
| 4,457,818 A | 7/1984 | Denyer et al. | 204/159.19 |
| 4,459,193 A | 7/1984 | Ratcliffe et al. | 204/159.23 |
| 4,468,251 A | 8/1984 | Hausselt et al. | 106/1.18 |
| 4,492,777 A | 1/1985 | Denton, Jr. et al. | 523/115 |
| 4,499,251 A | 2/1985 | Omura et al. | 526/278 |
| 4,512,340 A | 4/1985 | Buck | 128/90 |
| 4,514,342 A | 4/1985 | Billington et al. | 260/952 |
| 4,514,527 A | 4/1985 | Bowen | 523/115 |
| 4,515,930 A | 5/1985 | Omura et al. | 526/276 |
| 4,521,550 A | 6/1985 | Bowen | 523/116 |
| 4,525,256 A | 6/1985 | Martin | 204/159.18 |
| 4,529,384 A | 7/1985 | Severy | 433/213 |
| 4,537,940 A | 8/1985 | Omura et al. | 526/278 |
| 4,539,382 A | 9/1985 | Omura et al. | 526/276 |
| 4,540,722 A | 9/1985 | Bunker | 523/109 |
| 4,544,359 A | 10/1985 | Waknine | 523/116 |
| 4,544,467 A | 10/1985 | Bunker et al. | 204/159.24 |
| 4,547,531 A | 10/1985 | Waknine | 523/115 |
| 4,553,941 A | 11/1985 | Aasen | 433/228.1 |
| 4,588,756 A | 5/1986 | Bowen | 523/116 |
| 4,589,756 A | 5/1986 | Sqegusa | 354/432 |
| 4,593,054 A | 6/1986 | Asmussen et al. | 52/118 |
| 4,602,076 A | 7/1986 | Ratcliffe et al. | 522/7 |
| 4,612,361 A | 9/1986 | Peters | 528/185 |
| 4,629,746 A | 12/1986 | Michl et al. | 523/117 |
| 4,636,533 A | 1/1987 | Janda et al. | 522/14 |
| 4,640,936 A | 2/1987 | Janda et al. | 522/14 |
| 4,645,456 A | 2/1987 | James | 433/217.1 |
| 4,657,941 A | 4/1987 | Blackwell et al. | 522/14 |
| 4,659,751 A | 4/1987 | Bowen | 523/116 |
| 4,664,629 A | 5/1987 | Codkawski | 433/228.1 |
| 4,669,983 A | 6/1987 | Bunker | 433/217.1 |
| 4,670,576 A | 6/1987 | Bunker | 558/182 |
| 4,680,373 A | 7/1987 | Gallagher et al. | 528/185 |
| 4,705,836 A | 11/1987 | Ohtsuka et al. | 526/318.1 |
| 4,719,149 A | 1/1988 | Aasen et al. | 428/473 |
| 4,732,943 A | 3/1988 | Beech et al. | 525/303 |
| 4,746,686 A | 5/1988 | Waller | 522/14 |
| 4,755,620 A | 7/1988 | Iwamoto et al. | 560/224 |
| 4,794,157 A | 12/1988 | Berdahl et al. | 528/208 |
| 4,797,431 A | 1/1989 | Billington et al. | 523/116 |
| 4,806,381 A | 2/1989 | Engelbrecht et al. | 427/2 |
| 4,813,876 A | 3/1989 | Wang | 433/224 |
| 4,814,362 A | 3/1989 | Billington et al. | 523/117 |
| 4,816,495 A | 3/1989 | Blackwell et al. | 522/14 |
| 4,830,615 A | 5/1989 | Feinman et al. | 433/166 |
| 4,855,475 A | 8/1989 | Bunker | 558/182 |
| 4,861,808 A | 8/1989 | Billington et al. | 523/116 |
| 4,863,993 A | 9/1989 | Montgomery | 524/854 |
| 4,864,015 A | 9/1989 | Cella et al | 528/352 |
| 4,867,817 A | 9/1989 | Kneafsey et al. | 156/73.1 |
| 4,872,936 A | 10/1989 | Engelbrecht et al. | 156/307.3 |
| 4,880,660 A | 11/1989 | Aasen et al. | 427/2 |
| 4,913,939 A | 4/1990 | Montgomery | 427/389 |
| 4,918,136 A | 4/1990 | Kawaguchi et al. | 524/751 |
| 4,929,746 A | 5/1990 | Bunker | 558/92 |
| 4,945,006 A | 7/1990 | Muggee et al. | 428/500 |
| 4,948,366 A | 8/1990 | Horn et al. | 433/9 |
| 4,948,367 A | 8/1990 | Haas | 433/9 |
| 4,964,911 A | 10/1990 | Ibsen et al. | 106/35 |
| 4,966,934 A | 10/1990 | Huang et al. | 524/315 |
| 4,985,198 A | 1/1991 | Hirasawa et al. | 560/130 |
| 5,051,453 A | 9/1991 | Okabayashi et al. | 523/116 |
| 5,055,497 A | 10/1991 | Okada et al. | 523/116 |
| 5,063,257 A | 11/1991 | Akahane et al. | 523/116 |
| 5,064,495 A | 11/1991 | Omura et al. | 156/307.3 |
| 5,079,277 A | 1/1992 | Wilson et al. | 523/116 |
| 5,084,491 A | 1/1992 | Kerby | 523/116 |
| 5,085,726 A | 2/1992 | Omura et al. | 156/307.3 |
| 5,089,051 A | 2/1992 | Eppinger et al. | 106/35 |
| 5,091,441 A | 2/1992 | Omura | 523/109 |
| 5,130,347 A | 7/1992 | Mitra | 522/149 |
| 5,133,957 A | 7/1992 | Suh et al. | 424/49 |
| 5,141,436 A | 8/1992 | Orlowski | 433/226 |
| 5,154,762 A | 10/1992 | Mitra et al. | 106/35 |
| 5,171,763 A | 12/1992 | Ohno et al. | 523/116 |
| 5,177,121 A | 1/1993 | Bunker | 523/116 |
| 5,179,135 A | 1/1993 | Ellis et al. | 523/116 |
| 5,186,783 A | 2/1993 | Kawashima et al. | 156/307.3 |
| 5,189,077 A | 2/1993 | Kerby | 523/116 |
| 5,218,070 A | 6/1993 | Blackwell | 526/318 |
| 5,227,413 A | 7/1993 | Mitra | 523/116 |
| 5,234,972 A | 8/1993 | Saitoh et al. | 523/118 |
| 5,252,629 A | 10/1993 | Imai et al. | 523/118 |
| 5,254,198 A | 10/1993 | Kawashima et al. | 156/307.3 |
| 5,256,447 A | 10/1993 | Oxman et al. | 427/207.1 |
| 5,260,476 A | 11/1993 | Ohno et al. | 560/90 |
| 5,264,513 A | 11/1993 | Ikemura et al. | 526/318 |
| 5,270,351 A | 12/1993 | Bowen | 523/116 |
| 5,276,068 A | 1/1994 | Waknine | 522/28 |
| 5,295,824 A | 3/1994 | Wong | 433/9 |
| 5,295,825 A | 3/1994 | Betush | 433/28 |
| 5,304,585 A | 4/1994 | Bunker | 523/116 |
| 5,318,999 A | 6/1994 | Mitra et al. | 522/57 |
| 5,321,053 A | 6/1994 | Hino et al. | 522/26 |
| 5,338,773 A | 8/1994 | Lu et al. | 523/116 |
| 5,354,785 A | 10/1994 | Rheinberger et al. | 523/116 |
| 5,356,951 A | 10/1994 | Yearn et al. | 523/116 |
| 5,360,770 A | 11/1994 | Chadwick | 501/24 |
| 5,367,002 A | 11/1994 | Huang et al. | 523/116 |
| 5,401,783 A | 3/1995 | Bowen | 523/116 |
| 5,756,559 A | 5/1998 | Blackwell et al. | 523/115 |

FOREIGN PATENT DOCUMENTS

| | | |
|---|---|---|
| CA | 968741 | 6/1975 |
| CA | 969299 | 6/1975 |
| CA | 983190 | 2/1976 |
| CA | 1018294 | 9/1977 |
| CA | 1020687 | 11/1977 |
| CA | 1028441 | 3/1978 |
| CA | 1117242 | 1/1982 |
| CA | 1131388 | 9/1982 |
| CA | 1136796 | 11/1982 |
| CA | 1154895 | 10/1983 |
| CA | 1159984 | 1/1984 |
| CA | 1164124 | 3/1984 |
| CA | 1176787 | 10/1984 |
| CA | 1179094 | 12/1984 |
| CA | 1194637 | 10/1985 |
| CA | 1198847 | 12/1985 |

| | | |
|---|---|---|
| CA | 1200647 | 2/1986 |
| CA | 1213699 | 11/1986 |
| CA | 1216982 | 1/1987 |
| CA | 1243796 | 10/1988 |
| CA | 1244177 | 11/1988 |
| CA | 1259149 | 9/1989 |
| CA | 1261992 | 9/1989 |
| CA | 1262791 | 11/1989 |
| CA | 1262981 | 11/1989 |
| CA | 1269790 | 5/1990 |
| CA | 2009471 | 8/1990 |
| CA | 2011438 | 10/1990 |
| CA | 2038695 | 9/1991 |
| CA | 2051333 | 3/1992 |
| DE | 8708062 | 12/1987 |
| DE | 8801781 | 5/1988 |
| EP | 044701 | 1/1982 |
| EP | 0 241 277 A2 | 10/1987 |
| EP | 0 244 959 A2 | 11/1987 |
| EP | 0 323 120 A2 | 7/1989 |
| EP | 0 325 038 A3 | 7/1989 |
| EP | 0 329 268 | 8/1989 |
| EP | 0 335 645 A3 | 10/1989 |
| EP | 0 391 619 A3 | 10/1990 |
| EP | 0 470 446 A1 | 2/1992 |
| FR | 1069783 | 12/1952 |
| GB | 2 000 789 A | 1/1979 |
| GB | 2 156 347 A | 10/1985 |
| GB | 2 202 221 A | 9/1988 |
| WO | 80/00409 | 3/1980 |
| WO | 88/05651 | 8/1988 |
| WO | 93/12757 | 7/1993 |
| WO | 93/12758 | 7/1993 |
| WO | 93/12759 | 7/1993 |
| WO | 93/12760 | 7/1993 |
| WO | 93/14039 | 7/1993 |
| WO | 95/34270 | 12/1995 |

OTHER PUBLICATIONS

Antonucci et al, Polymer–Modified Glass Ionomer Cements, Journal Dental Research, vol. 68, p. 251, Abstract #555 (1989).

Rusz et al, Adhesive Properties of Polymer—and Resin–Modified Glass Ionomer Cements, Journal of Dental Research, vol. 69, p. 366, Abstract #2058 (1990).

Rusz et al, Adhesive Properties of Modified Glass–Ionomer Cements, Dental Materials, Jan. 1992, Adhesive properties of modified glass–ionomer cements.

Erickson et al, Evaluation of Experimental Fluoride–containing Restorative Materials, Journal of Dental Research, vol. 66, Special Edition, Mar. 11–15, 1987.

Prosser et al, Lith–ionomer Cements and their Technological Applications, J. Chem. Tech. Biotechnol 1979, 29, 69–87.

Wilson et al, Developments in Ionic Polymers–1, 1983, pp. 217–267.

Swartz et al, Long–Term F. Release from glass Ionomer Cements, Journal of Dental Research Feb. 1984/vol. 63/No. 2.

Erickson et al, Evaluation of Experimental Fluoride–Containing Restorative Material, 65th General Session, IADR, Mar. 11–15, 1987, Abstract No. 1114.

Heilmann et al, Chemistry of Alkenyl Azlactones. I. Radiation–Sensitive Materials Derived from Azlactone–Containing Copolymers, Journals of Polymer Science: Polymer Chemistry Edition, vol. 22 1179–1186 (1984).

Gunner Ryge, vol. 30, No. 4, Clinicla Criteria, pp. 347–358.

METHOD AND COMPOSITION FOR ADHERING TO METAL DENTAL STRUCTURE

This is a continuation of U.S. patent application Ser. No. 09/290,962 filed Apr. 13, 1999 which is a continuation-in-part of U.S. Ser. No. 09/080,781 filed May 18, 1998 now U.S. Pat. No. 6,191,190, which is a continuation-in-part of U.S. File Wrapper Continuation Ser. No. 08/627,339 filed Apr. 4, 1996, issued as U.S. Pat. No. 5,756,559, which is a continuation of U.S. patent application Ser. No. 08/292,104 filed Aug. 22, 1994, now abandoned and each of which is incorporated herein by reference in its entirety. This is a continuation in part of U.S. patent application Ser. No. 09/093,548 filed Jun. 8, 1998, now abandoned which is a continuation of U.S. patent application Ser. No. 08/995,997 filed Dec. 22, 1997, now U.S. Pat. No. 5,955,514, which is a continuation of U.S. patent application Ser. No. 08/259,833 filed Jun. 15, 1994 which is a continuation-in-part of U.S. patent application Ser. No. 08/049,221 filed Apr. 19, 1993 (1709) issued as U.S. Pat. No. 5,338,773 each of which is incorporated herein by reference in its entirety.

This invention relates to bonding compositions. In a preferred embodiment the invention provides an improved dental metal bonding composition. Beneficially the invention provides a single component adhesive system which bonds to dentin, to composite and to metal including metal and metal alloys used in dentistry. Preferred alloys used in dentistry contain at least 15 percent by weight of gold (Au), platinum (Pt), palladium (Pd) and/or silver (Ag), and are bonded to composite without leaving a gap at the bonding margin between the composite and the metal. Thus, the invention provides a one component self-priming light-curable adhesive for bonding composite materials to dental metals and dental alloys without the need for retention beads. Accordingly, the composition of the invention is useful for adhering crowns and bridges, inlays and onlays.

The invention relates to compositions for adhesion to teeth including dental primer, adhesive and composite filling material. The invention provides a composition and method of use thereof for adhering to dental tooth surface. The invention provides a dental composition including a polymerizable aryl compound having at least one carboxylic acid group and at least one polymerizable group and a polymerizable compound having at least one polymerizable group and at least one phosphorous containing group. One or more portions of the composition are applied and cured on a cleaned tooth surface to form a treated tooth surface. In a preferred embodiment of the invention, the composition is a priming adhesive or a restorative material which is applied to a dental tooth with a bond strength of at least about 12 MPa.

It is most desirable, when filling a tooth cavity with a filling material such as a polymerizable dental restorative, to ensure good adhesion between the tooth surrounding the cavity and the set (polymerized) filling material since there is thereby obtained a good seal between the set filling material and the tooth which prevents, or at least markedly inhibits, ingress of mouth fluids and bacteria into the filled cavity and thus prevents further decay or loss of the filling material. In order to achieve good adhesion between the filler material and the tooth enamel, it has been recommended to provide a primer or adhesive bonding layer intermediate the filling material and surfaces of a prepared tooth. The prior art does not disclose a shelf stable single component composition adapted to bond polymerizable acrylate containing restoratives to dentin with a bond strength of at least 12 MPa as is provided by the present invention.

Dental compositions in accordance with the invention are useful as dental primers and adhesives having unexpectedly superior adhesion to metal, dentin, enamel, cavity liner, bonding materials and filling materials.

It is an object of the invention to provide method of adhering a composite material to a dental metal by applying to the treated metal surface with or without retention beads a liquid composition including a polymerizable aryl compound, at least 50 percent by weight of volatile solvent, at least 15 percent by weight of one or more polymerizable acrylate compounds and effective amount of a photoinitiator, at least a portion of the polymerizable compounds being multifunctional polymerizable compounds having at least three acrylate moieties, to form a polymeric material which adheres to metal other than semiprecious and precious metals such as Au, Pt, Pd and Ag with a bond strength of at least 20 MPa.

It is an object of the invention to provide method of adhering a restorative material to a dental tooth by applying to the tooth a liquid composition including a polymerizable aryl compound, at least 50 percent by weight of a volatile solvent, at least 15 percent by weight of one or more polymerizable acrylate compounds and an effective amount of a photoinitiator, at least a portion of the polymerizable compounds being multifunctional polymerizable compounds having at least three acrylate moieties, to form a polymeric material which adheres to dentin with a bond strength of at least 12 MPa.

It is an object of the invention to provide a dental composition including a polymerizable aryl compound having at least one carboxylic acid group and at least one polymerizable group and a polymerizable compound having at least one polymerizable group and at least one phosphorous containing group.

It is the object of the invention to provide a restorative material bonded to nonprecious dental metal and alloy comprising for example Ti, Zn, Cu, Sn, Fe and/or Al (which are other than semiprecious and precious metals and alloys comprising at least 15% by weight of Au, Pt, Pd and/or Ag) with bond strength of at least 20 MPa.

It is the object of the invention to provide a restorative material bonded to Au, Pt, Pd and and/or Ag and alloys thereof with bond strength of at least 10 MPa.

It is an object of the invention to provide a restorative material bonded to the tooth with a bond strength of at least about 12 MPa.

It is an object of the invention is to provide new dental compositions useful as filling materials, cavity liners and bases, cements, and pit and fissure sealants other restorative materials which are adhesive to tooth structure.

It is the object of the invention to provide a composition that reduces the steps and time required to adhere composite materials to dental metals.

It is an object of the invention to provide a composition which reduces the steps and time required to adhere metal or ceramic to tooth structure.

It is an object of the invention to provide an adhesive composition for adhesion between composite restoratives and dental metal substrates.

It is an object of the invention to provide an adhesive composition for adhesion between tooth structure and/or bone and polymeric composites.

Volatile organic solvent(s) as used herein refers to organic solvent(s) which are substantially more volatile than water at 23° C. "Acrylate" as used herein refers to unsaturated polymerizable compounds within the general formula:

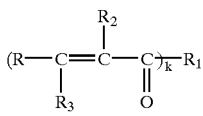

wherein, k is an integer from 1 to 8,
R is hydrogen or methyl,
$R_1$ is an alkyl having from 1 to 20 carbon atoms,
$R_2$ is an alkyl having from 1 to 8 carbon atoms, and
$R_3$ is an alkyl having from 1 to 12 carbon atoms.

"Polymerizable compound" as used herein refers to monomers and/or oligomers. Acrylates are preferred polymerizable compounds.

PENTA as used herein refers to 2,2,6-6 tetra acryloxyloxymethyl4, 8 dioxa-9-oxo-11-undecyl phosphoric acid, also known as dipentaerythritol pentacrylate phosphoric acid ester.

Phosphates as used herein does not include pyrophosphates.

"Monomer" as used herein means monomer or oligomer.

"Set" as used herein means a polymerizable composition undergoes a change so that it becomes firm, stiff and nonpliable.

As used herein "The MAX Lite" means THE MAX™, a curing unit for light-polymerizable dental materials sold by DENTSPLY International Inc. through its L.D. Caulk Division. Other curing units for light-polymerizable dental materials are Spectrum™ (sold by L.D. Caulk, a division of DENTSPLY International Inc.); Liculite (sold by DeTrey, a division of DENTSPLY International Inc.); Triad 2000 (sold by Trubyte, Division of DENTSPLY International Inc.); and Prismetics Lite (Sold by DENTSPLY International Inc.).

Throughout this disclosure unless otherwise specified amounts of each component of a composition are in percent by weight.

Relevant patents include U.S. Pat. Nos. 5,348,988; 4,755,620 and 5,564,030.

In the following Examples, Shear Bond Strength (SBS) is tested according to ISO 10477 using metal as substrate and composite restoratives as post. These methods were used to measure the bonding strengths of composites to precious metal alloys, non-precious metal alloys and other metal substrate by using compositions of present invention. Substrate Preparation: Prior to application of the adhesive composition, the surfaces of metal substrate were treated as follows. 1) Metal surfaces were polished with #320 and #600 grit SiC papers sequentially. 2) The polished surfaces were air abraded with 110 μm fresh aluminum oxide, and then cleaned with a dry hard brush. Bonding to dental alloys. 1) Dispense primer/adhesive into a clean mixing well. 2) Apply a generous amount of the adhesive over the entire bonding surface. 3) The surface remained fully wet for 20 seconds, and then air dry for 10 seconds. 4) Light cure the adhesive with curing unit. 5) Apply Licupast Opaquer two thin layer. For each layer, light cure with curing light unit (apparatus). 6) Incrementally place composites in two layers, and light cure the composites with curing unit. 7) Thermal cycle the bonding samples between 5° C. and 55° C. for 5000 cycles. 8) Test bonding strength using universal testing machine according to the ISO 10477.

Bond strength in units of MPa as used to herein unless otherwise indicated refers to bond strength measured as follows: uncontaminated, caries free, extracted human teeth without significant anatomical alterations, defects or restorations were cleaned and disinfected by soaking in 1% sodium hypo chlorite solution for 18 to 24 hours, rinsed with water and are then stored at from 1 to 8 C in 1% sodium chloride in water (saline solution) until used within six months. The wet teeth are then sanded flat by hand using wet 320 grit silicon carbide paper to expose an area of dentine at a plane just below the original interface between the enamel and the dentin, and this area of dentine is polished by hand with wet 600 grit silicon carbide paper. The teeth are kept wet in water until used within from 1 to 12 hours.

The dentin surface is dried lightly with a paper tissue, and the priming/adhesive solution of the invention applied in a thin layer using a dental operatory brush with bristles having a length of 5 mm and a diameter of 0.0025 inch. The solution is allowed to stand on the dentine surface for 20 seconds (unless otherwise noted) and the remaining solvent is evaporated by blowing the tooth gently with a stream of dry oil free air. The layer of primer/adhesive remaining is light cured by irradiating it for ten seconds (unless otherwise noted) with light from a dental light curing unit having a minimum output of 350 milliwatt/square centimeter in the 400 to 500 mm wavelength range (most preferably a Max lite, light curing unit, sold by DENTSPLY International, Inc., however in Examples 1 through 10 a Prismetics Lite, light curing unit, L.D. Caulk is used). A portion of plastic straw of 5mm internal diameter and about 4 mm long is placed end on to the prepared surface and filled with a light curing dental filling material (Dyract™, DeTrey DENTSPLY, Konstanz Germany unless otherwise noted). Finally the filling material is cured by irradiating with light from the dental light for forty seconds.

The prepared samples are stored for 24 hours in water at 37° C. before being thermocycled 500 times (unless otherwise noted) between 5° C. and 55° C. with a dwell time in each bath of 20 seconds. The thermocycled samples are left in water at 37° C. overnight before being tested in shear using a Zwick universal testing machine model 145501 with the load cell set for a maximum load of 500 Newtons, and operating at a crosshead speed of 1 mm per minute using a 2 mm diameter cylindrical chisel. The chisel has a tip point formed at the lower end by grinding and polishing a planar surface across the end of the cylinder at a 45 degree angle to the central axis of the cylinder. The tip point is formed at the intersection of a planar surface with the lower end of the chisel. In test position the tip point of the chisel is applied against the composite. Each tooth is vertically mounted in plastic for the test.

SUMMARY OF THE INVENTION

A composition and method of treating a dental tooth and a dental metal by applying a liquid composition to at least a portion of tooth or metal to form a treated surface. The composition includes a polymerizable aryl compound having at least one carboxylic acid group and at least one polymerizable group, and a polymerizable compound having at least one polymerizable group and at least one phosphorous containing group. A preferred composition includes at least 50 percent by weight of a volatile organic solvent, at least 15 percent by weight of one or more polymerizable acrylate compounds and an effective amount of a photoinitiator. At least a portion of the polymerizable compounds are multifunctional polymerizable compounds having at least three acrylate moieties. The polymerizable compounds are substantially soluble in the solvent. The composition is adapted to form a polymeric material which is adapted to adhere to dental metals and ceramics and to dentin. Compositions of the invention have superior adhesion to metals and to tooth without separately acid etching dentin or enamel. Compositions are useful as dental priming adhesives, metal bonding agents, luting cements, liners, pit and fissure sealants, bases and restoratives.

DETAILED DESCRIPTION OF THE INVENTION

A preferred embodiment of the invention provides a method of conditioning a tooth and/or metal surface including applying a first portion of a liquid priming adhesive composition to a cleaned tooth surface or a mechanically treated dental metal surface and curing the first portion of liquid primer adhesive composition to form a primed tooth surface. For adhering to tooth a second portion of the liquid priming adhesive composition may be then applied to the primed tooth surface and cured to form a conditioned tooth surface. A polymerizable restorative composition is bonded to metal substrates or the tooth with a bond strength of at least about 10 MPa, more preferably at least 12 MPa. Priming adhesive compositions useful in accordance with the invention preferably include in order of increasing preference at least 50, 60, 70 or 80 percent by weight of a volitile solvent and at least 15 percent by weight of a polymerizable compound.

In accordance with a preferred embodiment of the invention is provided a method of adhering a restorative material to a dental tooth or a dental metal by applying a dental composition which includes at least 50 percent by weight of a volatile solvent, at least 15 percent by weight of one or more polymerizable acrylate compounds and an effective amount of a photoinitiator. At least a portion of the polymerizable compounds are multifunctional polymerizable compounds having at least three acrylate moieties. A portion of the polymerizable compounds are aryl compounds. The polymerizable compounds are substantially soluble in the solvent. The composition is adapted to form a polymeric material which adheres to dental metals or dentin with a bond strength of at least 12 MPa.

Preferably the composition includes in order of increasing preference at least 2, 2.5, 3, 3.5, 4, 5, 6, 7, 8, 9 or 10 percent by weight of the multifunctional polymerizable compounds. Preferably the solvent is dimethyl ketone or methyl ethyl ketone and the bond strength is at least 15 MPa. Preferably the composition comprises at least 73 percent by weight of said solvent. Preferably at least a portion of the multifunctional polymerizable compounds are phosphate esters.

Preferably at least a portion of the multifunctional compounds have a chemical structure within the scope of the general formula:

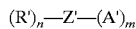

wherein each R' independently is an acrylate containing moiety, Z' is an organic moiety, each A' is independently is a phosphorous containing, group such as a phosphate or a phosphate salt, n is an integer greater than 2, m is an integer of 1 or more Preferably at least a portion of the polymerizable compounds are acids and the acids comprise at least 2 percent by weight of the composition. Preferably at least a portion of the polymerizable compounds are acid esters.

In accordance with a preferred embodiment of the invention is provided a method of treating a dental tooth or dental metal (alloys) by applying a first portion of a liquid composition to a dental tooth or a treated dental metal surface. The polymerizable compounds in the first portion of the liquid composition are cured polymerized) to form a primed tooth surface.

In accordance with a preferred embodiment of the invention is provided a method of adhering a restorative material to a dental tooth or a metal by applying a liquid composition to at least a portion of the tooth or the metal to form a treated surface. The composition includes at least 50 percent by weight of a volatile solvent, at least 15 percent by weight of one or more polymerizable acrylate compounds and an effective amount of a photoinitiator. At least a portion of the polymerizable compounds are multifunctional polymerizable compounds having at least three acrylate moieties. The polymerizable compounds are substantially soluble in the solvent. The composition is adapted to form a polymeric material which is adapted to adhere to metal or dentin with a bond strength of at least 12 MPa. Restorative material is then affixed to at least a portion of the treated surface with a bond strength of at least about 12 MPa.

Acid-etching of enamel may be done but is not necessary. To fill deep tooth cavities it is preferred to cover the dentine closest to the pulp of the tooth with a hard-setting calcium hydroxide liner (such as DYCAL, sold by DENTSPLY International Inc.) leaving the rest of the cavity floor and walls free for chemical bonding with a dental restorative such as Dyract, sold by DENTSPLY International Inc.

Preferred volatile solvents include, ethanol, methanol, isopropanol, dimethyl ketone, ethylmethyl ketone, and mixture of these.

Preferred monomers for use in primer adhesive compositions in accordance with the inventor have a solubility in water of less than about 5%, and more preferably have a solubility in water of less than 1%. Exemplary monomers include triethylene glycol dimethacrylate, tetraethyleneglycol dimethacrylate, glycerol-1,2-dimethacrylate, glycerol-1,3-dimethacrylate, the reaction product of butanediol diglycidyl ester and methacrylic acid, tetrahydrofurfural methacrylate, methacryloxyethyl maleic ester, methacryloxyethyl succinate, urethane dimethacrylate, Bis-GMA, Ethoxylated bisphenol-A dimethacrylate, bisphenol-A dimethacrylate, and mixtures thereof. Monomers having a solubility in water higher than 5% are less preferred. Monomer having a solubility in water less than about 1% are more preferred. Highly water soluble monomers such as hydroxyethyl methacrylate and hydroxypropyl methacrylate tend to provide lower adhesion and are less suitable for use in compositions of the invention.

A volatile solvent is removed after application of the primer of the dentin or metal surface. The monomer is preferably less volatile than the solvent.

In use, compositions of the invention are preferably applied to a sandblasted clean dental metal surface or a clean dry dentine surface, and the solvent is evaporated, for example, by application of a gentle stream of air. The layer of resin remaining is preferably cured by exposing it to light from a dental curing lamp. The composite filler formation is then applied by exposing it to light from a dental curing lamp and cured.

Prior art dentine adhesive systems giving adhesion higher than 12 MPa have required separate applications of a primer composition and an adhesive composition. The combined primer/adhesive composition of the present invention achieves high bond strength adhesion levels with application of one liquid.

In addition, the combined primer/adhesive compositions of the present invention also achieves high metal adhesion level with application of one liquid without use of retention beads.

As the free radical-polymerizable monomer or prepolymer to be employed in this invention, use may be made of any monomer, dimer, trimer, or other oligomer of the type that is usable in dental applications. Thus, the polymerizable monomer portion of the present adhesive composition generally comprises one or more monofunctional or polyfunctional ethylenically unsaturated monomers or prepolymers, e.g., dimers, trimers, and other oligomers, or mixtures or copolymers thereof, based on acrylic or methacrylic or itaconic acid, or derivatives thereof, including their esters which can be polymerized by free radical initiation. These materials include, but are not limited to acrylic and methacrylic acid, itaconic acid and the like, acrylic or methacrylic or itaconic acid esters of monohydric or polyhydric alkanols or polyhydric alcohols containing at least one phenyl group. Examples of such compound include monovinylmethacrylates, e.g., methylmethacrylate, ethyl acrylate, propyl methacrylate, hydroxyethylmethyacrylate, hydroxypropylmethacrylate, diethylene glycol acrylate, triethylene glycol acrylate, the monoester of trimellitic acid with hydroxyethyl methacrylate, hydroxypropyl itaconate and the like, esters of aliphatic polyhydric alcohols, such as for example, the di- and polyacrylates, the di- and polymethacrylates, and the di- and polyitaconates of alkylene glycols, alkoxylene glycols, alicyclic glycols and higher polyols, such as ethylene glycol, triethylene glycol, tetraethylene glycol, tetramethylene glycol, trimethylolethane, trimethylolpropane, pentaerythritol, dipentaerythritol, tripentacryritol, and the like, or mixtures of these with each other or with their partially esterified analogs, and their prepolymers, such compound or mixture optionally having free hydroxyl content. Typical compounds of this type, include but are not limited to, trimethylolpropane triacrylate, trimethylolethane triacrylate, trimethylolpropane trimethacrylate, trimethylolethane trimethacrylate, tetramethylene glycol dimethacrylate, ethylene glycol dimethacrylate, triethylene glycol dimethacrylate, tetraethylene glycol diacrylate, tetraethylene glycol dimethacrylate, pentaerythritol diacrylate, pentaerythritol triacrylate, pentaerythritol tetraacrylate, dipentaerythritol diacrylate, dipentaerythritol triacrylate, dipentaerythritol tetraacrylate, dipentaerythritol pentaacrylate, dipentaerythritol hexacrylate, tripentaerythritol octaacrylate, pentaerythritol dimethacrylate, pentaerythritol trimethacrylate, dipentaerythritol dimethacrylate, glycerin trimethacrylate, ethylene glycol dimethacrylate, butanediol dimethacrylate, trimethylolpropane trimethacrylate, tetramethylolmethane tetramethacrylate,bisphenol-A dimethacrylate, bisphenol-A diglycidyl methacrylate, 2,2, '-bis-(4methacryloxyethoxyphenyl) propane and so on.

Also included among the polymerizable monomers which may be used are the vinyl urethane or urethane-acrylate prepolymers which are well known in the art. These prepolymers are polymerizable by free radical initiation and may be prepared, for example, by reacting an organic diisocyanate or an isocyanate-terminated urethane prepolymer with an ethylenically unsaturated monomer which is reactive with the diisocyanate or urethane prepolymer. These polymers also may be prepared by reacting a hydroxyl-containing material, such as a polyol or a hydroxyl-terminated urethane prepolymer with an ethylenically unsaturated monomer which is reactive with the polyol or hydroxyl-terminated urethane. The urethane prepolymers, which may be linear or branched, carry isocyanate end groups and generally are prepared by reacting a compound having hydroxyl functionality with a molar excess of diisocyanate.

Any of a wide variety of diisocyanates may be used to prepare the isocyanate-terminated urethane prepolymer including aliphatic, cycloaliphatic, heterocyclic, and aromatic diisocyanates, and combinations of these. Examples include, but are not limited to, 2,4tolylene diisocyanate, 2,6-tolylene diisocyanate, 1,4-phenylene diisocyanate, 2,2,4-trimethyl hexamethylene diisocyanate, hexamethylene diisocyanate, 1,4-naphthalene diisocyanate, 1,5-naphthalene diisocyanate, 4,4, '-diphenylmethane diisocyanate, p,p,'-diphenyl diisocyanate, butylene-1, '-diisocyanate, ethylene diisocyanate, trimethylene diisocyanate, tetramethylene-1, 4diisocyanate, butylene-2,3-diisocyanate, cyclohexylene-1, 2-diisocyanate, methylene-bis-(4-phenyl-isocyanate), diphenyl-3,3, '-dimethyl-4,4, '-diisocyanate, xylylene diisocyanate, cyclohexane-1,4-diisocyanate, 1-methoxyphenyl-2,4-diisocyanate and the like, and mixtures thereof.

A wide variety of compounds having hydroxyl functionality may be used to form the isocyanate-terminated urethane prepolymers. For example, diols of the structure

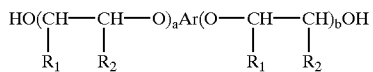

may be used, where R1 and R2 are hydrogen atoms or alkyl groups, e.g., methyl, and Ar is a divalent aromatic group in which each free valency is on an aromatic carbon atom, and where a and b, independently, may be zero or an integer. Other suitable hydroxyl containing compounds include diols and polyols such as ethylene glycol, propylene glycol, triethylene glycol, tetramethylene glycol, trimethylolpropane, pentaerythritol, dipentaerythritol, and the like, or esters of acrylic acid, methacrylic acid or itaconic acid or the like with aliphatic polyhydric alcohols. Among the more preferred hydroxyl containing compounds are the esters of acrylic or methacrylic acid and a hydroxyalkanol of at least two carbon atoms such as hydroxyethyl acrylate, hydroxyethyl methacrylate, hydroxypropyl acrylate, hydroxypropyl methacrylate, hydroxyisopropyl methacrylate, and the like.

Formation of the isocyanate terminated urethane prepolymers may be assisted by the use of a catalyst known in the art to assist polyurethane formation, for example, tertiary amines and metal salts, e.g., tin salts, titanium salts and the like.

To form the vinyl urethane or urethane-acrylate prepolymer starting materials, an isocyanate-terminated urethane prepolymer or diisocyanate is reacted with an ethylenically unsaturated compound having hydroxyl functionality. These compounds include for example, esters of acrylic acid, methacrylic acid or itaconic acid with aliphatic polyhydric alcohols, such as hydroxyethyl acrylate, hydroxypropyl methacrylate or the like. The resulting vinyl urethanes are well known in the art and are described for example, in U.S. Pat. No. 3,629,187 to Waller, U.S. Pat No. 3,759,809 to Carlick et al, U.S. Pat. No. 3,709,86 to Waller and U.S. Pat No. 4,459,193 to Ratcliffe et al, and all of these patents are incorporated herein by reference.

With a preferred embodiment of the invention two or more ethylenically unsaturated compounds are included in dental treatment compositions. In a preferred embodiment of the invention the polymerizable monomer is liquid at temperatures from about 20° C. to about 25° C.

Preferred monomer are TEGDMA, glyceryl dimethacrylate, polyethylene glycol dimethacrylate, trimethylolpropane, trimethacrylate, UDMA, R5-62-1, EBPDMA, and ethylene glycol dimethacrylate.

Preferred solvents are ethanol, 2-propanol, and dimethyl ketone.

A preferred bonding composition in accordance with a preferred embodiment of the invention includes 5–10 percent by weight of PENTA; 5–10 percent by weight OEMA, 10–13 percent by weight of urethane diacrylate; 0–25 percent by weight of TEGDMA; 0 to about 1 percent by weight of glutaraldehyde; 0.2 percent by weight of camphorquinone (CQ); 0.4–0.6 percent by weight of EDAB; 0.1 percent by weight of BHT; from 80.8 to about 73.5 percent by weight of dimethyl ketone.

A preferred etchant includes 10 percent by weight of $H_3PO_4$; 25 percent by weight of $AlCl_3$; 87.5 percent by weight of water.

Exemplary acrylic monomers for use in compositions of the invention include: 1,4-butanediol dimethacrylate (BDEM); glyceryl dimethacrylate (GlyDM); hydroxyethyl methacrylate (HEMA); triethyleneglycol dimethacrylate (TGD); tetrahydrofuran dimethacrylate (THEMA).

In accordance with a preferred embodiment of the invention is provided a polymerizable composition which includes a polymerizable aryl compound having a moiety having at least one acid group and at least one polymerizable group. More preferably each of the polymerizable aryl compounds is within the scope of the general formula (B1)

$$(Y'')_o(B'')_s(A'')_p \quad (B1)$$

wherein each Y" independently is a polymerizable group, each A" independently is an acid group, each B" independently is a organic moiety, and o, p, and s each independently is a number having an average value of at least 1. Preferably the composition is adapted to not set for at least 24 house in the absence of polymerization initiation.

The invention provides a polymerizable composition which includes a polymerizable salt (complex) within the scope of the general formula (C1) and/or a novel material within the scope of the general formula (C2):

$$[(Y'')_o(B'')_s(A'')_p]_r\text{—}(M'')_q \quad (C1)$$

$$[[(Y'')_o(B'')_s(A'')_p]_r\text{—}(M'')_q]_t\text{—}P'' \quad (C2)$$

wherein each Y", A" and B" a as defined above and, each M" independently is a multivalent cation which forms a complex by bonding to one or more A"; P" is a particle and o, p, q, r, s, and t each independently is a number having an average value of at least 1. Preferably M" is a multivalent ion of a glass particle. This composition is adapted to not set for at least 24 hours in the absence of polymerization initiation.

Compounds within the scope of general formula, B1, preferably have molecular weights less than 100,000; more preferably less than 20,000 and most preferably less than 5,000 and especially preferred are such complexes having molecular weights less than 1,000.

Dental compositions of the invention preferably include polymerizable unsaturated substituted aromatic compounds within the scope of the general formula (I):

(I)

[structure: aromatic rings with $R_1$, $Z_1$, n, X, m, $Z_2$, $R_2$]

-continued wherein X is O, S, $\underset{O}{\overset{O}{\underset{\|}{\overset{\|}{S}}}}$, $\underset{\overset{\|}{O}}{\overset{O}{\underset{\|}{S}}}$, $\underset{R_4}{\overset{R_9}{N}}$, $\underset{R_{11}}{\overset{R_{10}}{P}}$, $\underset{OR_{12}}{\overset{OR_{13}}{P}}$, $\underset{\overset{\|}{O}}{\overset{O}{\underset{\|}{P}}}$, $\underset{\overset{\|}{O}}{\overset{O}{\underset{\|}{P}}}$, $O\text{—}\overset{O}{\underset{\|}{\overset{\|}{P}}}\text{—}O$, $\underset{R_4}{\overset{R_3}{\underset{|}{\overset{|}{C}}}}$, or $(O)_a\text{—}[(\overset{R_5}{\underset{R_6}{C}})_b\text{—}O]_p$ wherein $R_1$ and $R_2$ each independently is a polymerizable unsaturated moiety having from 2 to 13 carbon atoms, $R_3$, $R_4$, $R_5$, and $R_6$ each independently is hydrogen, halogen, alkyl having from 1 to 10 carbon atoms or halogenated alkyl of from 1 to 10 carbon atoms, $R_9$, $R_{10}$, $R_{11}$, $R_{112}$, $R_{13}$ and $R_{14}$ each independently is hydrogen, alkyl having 1 to 10 carbon atoms or aryl having from 6 to 10 carbon atoms, $Z_1$ and $Z_2$ each independently is a moiety including an acid group, a, m and n each independently is 0 or 1, b, and p independently is an integer from 1 to 10, is from 1 to 3, and Dental compositions of the invention include polymerizable unsaturated substituted aromatic complexes within the scope of the general formula (IA):

(IA)

$$\left[R_1 \underset{Z_1}{\overset{}{\bigcirc\bigcirc}}_n X \underset{Z_2}{\overset{}{\bigcirc\bigcirc}}_m R_2\right]\text{—}M$$

wherein X, $R_1$ and $R_2$, $R_3$, $R_4$, $R_5$, $R_6$, $R_9$, $R_{10}$, $R_{11}$, $R_{12}$, $R_{13}$, $R_{14}$, $Z_1$ and $Z_2$, a, m, n, b, and p, are as defined above and M is a multivalent cation which reacts with acid moieties to form a complex.

In accordance with a preferred embodiment of the invention $R_1$ and $R_2$ each independently is:

$$\text{—}\overset{O}{\underset{\|}{C}}\text{—}R_7\text{—}O\text{—}\overset{O}{\underset{\|}{C}}\text{—}\underset{R_8}{\overset{|}{C}}\text{—}CH_2$$

wherein $R_7$ a divalent carbon containing radical and $R_8$ is hydrogen, halogen or alkyl having from 1 to 10 carbon atoms.

In a preferred embodiment of the invention compounds are provided within the scope of general formula I wherein n and m are zero, X is oxygen, sulfonyl or ditrifluoromethyl, and $R_1$ and $R_2$ are $$\text{—}\underset{\overset{\|}{O}}{\overset{}{C}}\text{—}O\text{—}CH_2\text{—}CH_2\text{—}O\text{—}\overset{O}{\underset{\|}{C}}\text{—}\underset{CH_3}{\overset{|}{C}}\text{=}CH_2$$

Most preferably compound within the scope of general formula I are those wherein X is oxygen or ditrifluoromethyl, and M is barium, calcium, strontium or aluminum. Preferred polymerizable unsaturated groups $R_1$ and $R_2$ independently are alkenyl, alkenoxy, cycloalkenyl, arylalkenyl, and alkenaryl moieties; with vinyl, and styryl moieties being more preferred, and acryl and methacryl moieties that constitute the polymerizable groups of many monomers in dental materials being especially preferred. Exemplary $R_1$ and $R_2$(meth)acrylate moieties include:

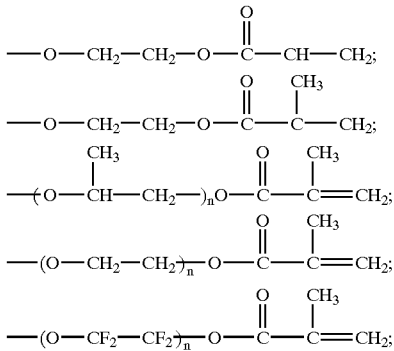

where n preferably is an integer from 1 to 10. Preferably RI and $R_2$ are (meth)acryloyloxyethyl moieties.

Preferred compounds for use in complexes within the scope of formula 1 include diesters which are the adducts of 2,2-bis(3,4-dicarboxylphenyl) hexafluoropropane anhydride, 4,4'-oxydiphthalic anhydride, 4,4'-sulfonyldiphthalic anhydride, respectively with 2-hydroxyethyl methacrylate. In a preferred embodiment at least two aromatic rings of a compound for use in complexes with the scope of formula 1 are joined through at least one saturated carbon, oxygen or sulfonyl.

Aromatic dianhydrides preferred for making compounds for use in complexes within the scope of general formula 1 react to form partial esters and carboxylic acid functionality. Dianhydrides having at least two aromatic rings are more preferred. Most preferably at least two aromatic rings are joined as shown in formula 1 to provide disruption of conjugation between the aromatic rings. It has been found that such compositions are less sensitive to light induced changes in color, and are therefore preferred when esthetic considerations are of importance. Most preferred examples are 4,4'-oxydiphthalic anhydride and 2,2-bis(3,4-dicarboxyphenyl)hexafluoropropane dianhydride.

Dental compositions in accordance with a preferred embodiment of the invention include an acid functional polymerizable organic ester for use in complexes within the scope of general formula I, water, cation elurable glass filler, and a polymerization catalyst system. Optionally, additional polymerizable monomers and/or prepolymers are included.

A composition in accordance with a preferred embodiment of the invention provides polymerizable monomer having at least one acid radical or reactive d derivative, and a source of cations reactive with the acid moiety, and a catalyst system. Preferably the catalyst system promotes free radical polymerization and preferably includes visible light curing and/or catalyst system. Preferably the composition includes liquid diluents, and/or filler adjuvants. Diluent preferably co-polymerizes with the polymerizable monomer within the scope of general formula AI. Alternatively the diluent is nonreactive with the polymerizable monomer. Water or low boiling alcohols such as methanol, ethanol and isopropanol are nonreactive diluents. Suitable polymerizable co-monomers are disclosed in U.S. Pat. No. 4,657,941 particularly at column 3 line 5 through column 5 line 59 and U.S. Pat. No. 4,514,342 both of which are incorporated herein by reference. The filler adjuvants are preferably reactive, for example by providing a source of cations which are reactive with the acid moiety of the polymerizable monomer. Nonreactive filler is preferably included in compositions in accordance with a preferred embodiment of the invention. Optionally, fillers have surface treatments to improve compatibility and strength of the resulting composition. Exemplary fillers include silica, silicates, alumina, aluminates, calcium fluoride, strontium fluoride, glasses including fluorine glasses, ceramics and minerals including mica, zeolites, ceramics, calcium apatites and organic polymer and those disclosed in U.S. Pat. Nos. 4,759,612 and 5,079,277.

The compounds within the scope of general formula BI have at least two different functional substituent groups, one of which is capable of addition polymerization and the other of which is carboxyl or other acid or reactive acid derivative. Most preferably these compounds include at least one polymerizable group and one or more acid or reactive acid derivative groups. Preferred compounds within the scope of general formula AI are derived acid formed from the reaction of 4,4'-oxydiphthalic anhydride or 2,2-bis(3,4-dicarboxylphenyl)hexafluorpropane dianhydrides with a polymerizable hydroxyl or polyhydric compound to form esters and partial esters thereof.

The new salt compounds of the invention are capable of being polymerized to form linear or crosslinked polymers which contain multiple acid groups or reactive acid derivative groups that have been reacted with cations, especially those of valence 2 or greater to form poly-salts. Because the salt compounds are monomers of relatively low molecular weight with a high density of both ethylenic unsaturation and carboxylic reactive acid derivative sites, excellent curing with superior integrity occurs. The carboxyl group itself is most preferred over other acid moieties or the reactive acid derivative ions. Especially appropriate acid moieties are all those that react with oxidic, mineral, ceramic, vitreous or metallic fillers.

Examples of these other acid moieties include:

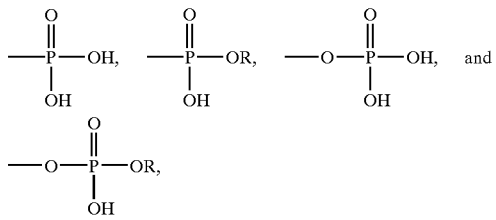

of phosphorous acids wherein R is alkyl, aryl, or vinyl; the moieties —$SO_2H$, $SO_3H$, or —O—$SO_3H$ of sulfuric acids;
the moieties:

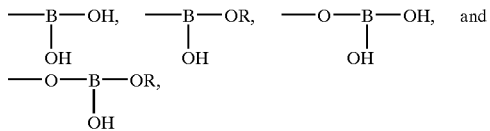

of boron acids wherein R is alkyl, aryl, or vinyl and cationic acid moieties including —$NR_2H+$ wherein R is H or alkyl. The reactive acid derivatives can be substituted with acid halides, with acid anhydrides, and with acid amides, nitrites, and esters that readily hydrolyze into acid, such as can enter into ion-exchange, neutralization, salt formation, or chelation reactions with the reactive filler. Preferred acid or reactive acid derivatives are carboxylate, phosphate, phosphonate, sulfonate, or borate acid moieties and/or of their reactive derivatives.

The compositions of the invention are formulated as one, two or more components, visible light curable, self cure, and/or dual cure product or combinations of these. The composition of a preferred embodiment of the invention includes polymerizable carboxylic acid monomer, an optional filler and/or diluent, a cationic elutable glass or other source of polyvalent cations, and a polymerization catalyst system. The polymerizable carboxylic acid monomers are chosen to provide a suitable balance of hydrophobic and hydrophilic moieties in order to provide a balanced set of properties including adhesion to metal, ceramics and tooth. They are essentially non-volatile and not critically affected by moisture during hardening within the oral cavity; and provide the ability to be used on hydrated surfaces such as found on and in teeth; and in a preferred embodiment do not require the separate steps of acid etching and adhesive priming to achieve adhesion to tooth structure.

For a better understanding of the characteristics and method of producing the preferred ethylenically unsaturated carboxylic compounds for use in complexes of the present invention the preparation of a preferred series of the compounds is carried out as follows:

In the presence of acid, base or other suitable catalyst one mole 4,4'-oxydiphthalic anhydride is reacted with two moles of a compound of the general formula R—OH, wherein R is a polymerizable unsaturated moiety having from 2 to 13 carbon atoms. This yields a liquid product which is believed to be a mixture of isomer monomers of general formulas I–IV:

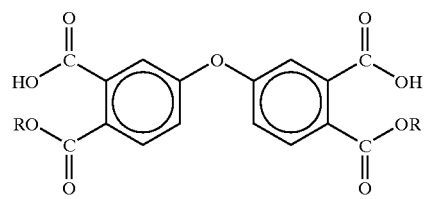

(II)

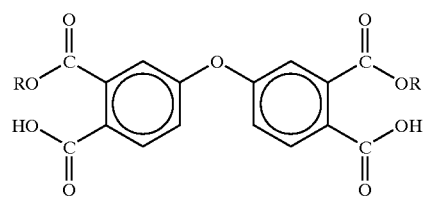

(III)

and

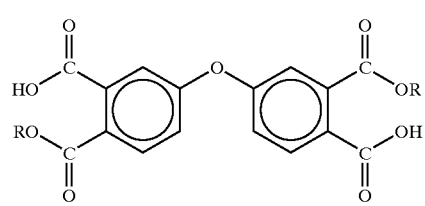

(IV)

As discussed in detail in Example 15 by reacting one mole of oxydiphthalic anhydride with two moles of methacryloxyethyl alcohol also known as 2-hydroxyethyl methacrylate (HEMA) in the presence of catalyst a liquid product is formed which is believed to be a mixture of isomer monomers V–VII:

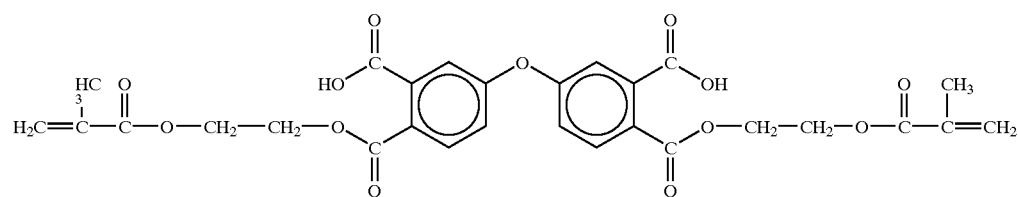

(V)

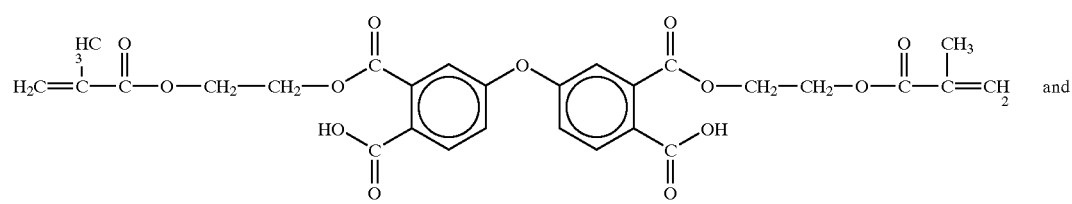

(VI)

and

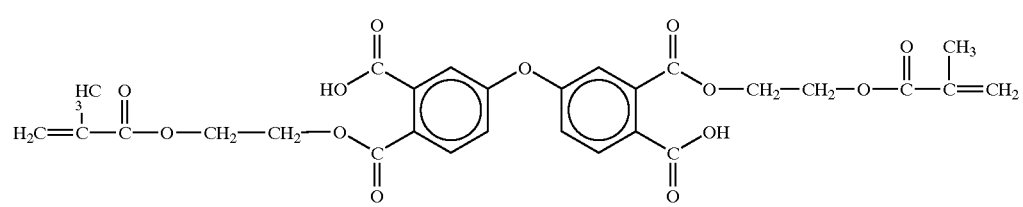

(VII)

Monomer compounds for use in complexes within the scope of general formula I are reactive esters which have at least one unreacted carboxylic acid group and one polymerizable group in the monomer. The number of reacted or unreacted carboxylic acid groups in the monomer is controlled by varying the reaction conditions and molar ratio of reactants. The monomer compounds of the invention polymerize by addition polymerization through the ethylenically unsaturated group. Curing agents, catalysts, initiators aid/or accelerators, are used to expedite and control the polymerization. A peroxide initiator, for example benzoyl peroxide, and/or heat are useful to initiate the reaction. Accelerators enhance the reaction so that it may proceed more expeditiously at room temperature. Accelerators preferably include reducing agents such as amines or sulfinates, and/or transition metal ions. Ultraviolet and/or visible light are used with initiators and accelerators to initiate and accelerate the polymerization. Visible light curing is preferred for curing the compositions of the invention in the mouth. For preformed objects, or those cured outside the body, other forms of radiation, for example ultraviolet ionizing radiation is preferred for curing the compositions of the invention.

In accordance with the method of the invention in-vivo polymerization does not harm the patient within whom polymerization of monomer compound (or complexes) within the scope of general formula I occurs. Preferably a single part composition is induced to polymerize by the application of heat or light. To initiate by irradiation with ultraviolet or visible light the initiator, for example a benzophenone or camphorquinone is preferably used to form a single, premixed, ready to use shelf-stable composition. A preferred embodiment of the composition of the invention includes a polymerization catalyst system having a light sensitive polymerization initator such as camphorquinone, a reducing agent such as ethyl 4-dimethylaminobenzoate (EDAB) and an oxidizing agent such as benzoyl peroxide. Redox polymerization systems known to the art are preferably used to polymerize the composition of the invention. Preferred redox polymerization catalyst systems for use in accordance with the invention include, a peroxide and tributyl boron and/or a transition metal salt. Redox polymerization catalysts and catalyst systems are those disclosed in U.S. Pat. No. 4,657,941 at column 7 line 10 through column 8 line 27 incorporated herein by reference. A particular polymerization method and system may be preferred depending on the application requirements of the material. Whatever the mode of polymerization, or "set or cure" of the composition including the salt monomers, an important characteristic of the polymers which form is that they have been prereacted with di- or polyvalent cations. The salt compounds and compositions of the invention exhibit adhesion between the resin and a cation containing surface, metal metal oxide, tooth and/or bone against which they are polymerized.

Fillers which are especially suited for use in composite and/or pit and fissure sealant compositions of the invention are inorganic glasses such as are used m glass ionomer cements. Exemplary of such fillers are those of U.S. Pat. No. 4,814,362 which is incorporated herein by reference in its entirety. Preferred fillers are glasses formed from or including, barium, calcium, strontium lanthanum, tantalum, and/or tungsten silicates and aluminates and/or aluminosilicates, silica, including submicron silica, quartz, and/or ceramics for example, calcium hydroxy apatite. In a preferred embodiment of the invention reactive cations, especially those of calcium, strontium and aluminum, and anions especially fluoride ions; are eluted from the fillers.

The fillers used in the invention preferably are reduced in particle size and in a preferred embodiment are silanated before they are incorporated into such compositions. Preferred levels of filler are from about 20% to about 85% based on the total weight of the cement composition, with from about 40% to about 85% being more preferable and about 50–80% being most preferred. If a more finely particulated filler is used, amounts of filler may be decreased due to the relative increase in surface, area which attends the smaller sizes of particles. Preferred particle size distributions are from 0.02 to 50 microns, more preferably 0.1 to 10 microns, and most preferably 1 to 6 microns.

In a preferred embodiment of the invention the cations of the salts are di- and polyvalent cations, such as Sr, Ca Al and Ba. In another preferred embodiment compositions of the invention include solvents, plasticizers, pigments, antimicrobials and therapeutics which may be time released from the composition, and oxidation inhibitors such as butylated hydroxytoluene. In addition to compounds within the scope of general formula I compositons in accordance with the invention preferably include polymerizable unsaturated diluent monomers, oligomers and/or prepolymers that do not contain any acid groups and/or salts thereof and/or reactive readily hydrolyzing acid-derivative groups thereof. One such preferred monomer is hydroxyalkyl methacrylates. Compositions of the invention may also preferably include compounds having acid groups and/or their salts and/or their readily reactive hydrolyzing derivative groups but do not contain any groups that are unsaturated and polymerizable, such as multi-basic acids or their reactive, readily hydrolyzing derivative. Especially preferred multibasic acids are hydroxy acids such as tartaric or citric acid.

Compounds that have chelating groups but do not contain carboxylic acid groups or readily hydrolyzing acid-derivative groups are preferably included in composition in accordance with the invention, for example vanillates, syringates, and salicylates.

Mixing the compositions of the present invention may be achieved using standard compounding techniques. For example, liquids, photoinitiator(s), and accelerator(s) are blended fist, and fillers are added incrementally thereafter. When blending light sensitive compositions, however, a photosafe room illumination, i.e., one that does not contain substantial amounts of wavelengths of electromagnetic radiation that would activate the photoinitiating system is used to avoid initiating polymerization of the composition prematurely.

PIT AND FISSURE SEALANTS

In a preferred embodiment of the invention a one or two component pit and fissure sealant which includes a polymerizable compound having at least three acrylate moieties and at least one compound within the scope of general formula I is applied to anatomic defects and/or the exterior of teeth. The sealant limits the ability of caries-forming bacteria to colonize the pits, fissures and other surfaces of the teeth. Pit and fissure sealant compositions in accordance with the invention are an especially valuable means of reducing caries by filling and eliminating enamel defect. The pit and fissure sealants of the invention are preferably applied without prior acid etching or the use of rubber dam to teeth. In one embodiment fluoride eluting compounds and glasses are preferably included in compositions of the invention. Fluoride is eluted to reduce the incidence of caries in tooth substance adjacent the compositions of the invention.

In accordance with the method of a preferred embodiment of the invention cement and restorative compositions include at least one polymerizable acid reactive ethylenically unsaturated compound within the scope of general formula I. Such compositons are applied to tooth without prior etching of the tooth.

In a preferred embodiment the invention provides a primer/bonding-resin composition comprising (A) a polymerizable resin component comprising a mixture of (i) at least one of a hydrophilic primer monomer having at least one carboxylic acid group and at least one polymerizable vinyl group, the primer monomer comprising a reaction product of at least one of an anhydride and a dianhydride compound with a compound having at least one vinyl group and at least one hydroxyl group, (ii) at least one high viscosity bonding resin compound having at least one reactive vinyl group, and (iii) a reactive monomer for diluting a viscosity of at least one of the high viscosity bonding resin compound and the hydrophilic primer monomer, the reactive monomer having at least one vinyl group reactive with at least one of the high viscosity bonding resin and the hydrophilic monomer, (B) a photo-initiator system for initiating polymerization of the resin component with the system is combined with the resin component and exposed to activating radiation; and (C) a solvent for dissolving or suspending the resin component and the photo-initiator system in a flowable form, wherein the resin component, the photo-initiator system and the solvent are selected so that a mixture thereof results in a shelf stable composition substantially polymerizable upon exposure of said mixture to at least one of an activating radiation and external polymerization catalyst. Preferably, the high viscosity bonding resin compound is 2,2-bis[4-(2-hydroxy-3-methacryloxypropoxy)phenyl] (Bis-GMA), 2,777,9,15-pentamethyl-4,13-dioxo-3,14-dioxa-5,12-diaza-hexadecane-1,16-diyl dimethacrylate (UDMA), or mixtures thereof. Preferably, the reactive monomer for diluting the viscosity of the high viscosity bonding resin compound is HEMA. Preferably, the photo-initiator comprises camphorquinone. Preferably, solvent is ethanol. Preferably, the solvent is selected from the group consisting of water and ethanol. Preferably, the bonding resin is an oligomer or prepolymer.

A preferred embodiment of the invention provides a composition comprising (A) a polymerizable component comprising a mixture of (i) at least one of a first monomer having at least one carboxylic acid group and at least one polymerizable vinyl group, the first monomer comprising a reaction product of at least one of an anhydride and a dianhydride compound with a compound having at least one vinyl group and at least one hydroxyl group, (ii) at least one high viscosity bonding resin compound having at least one reactive vinyl group, and (iii) a second monomer for diluting the viscosity of at least one of the high viscosity bonding resin compound and the first monomer, the second monomer having at least one vinyl group reactive with at least one of the high viscosity bonding resin and the first monomer; (B) a photo-initiator system for initiating polymerization of the resin component with the system is combined with the resin component and exposed to activating radiation; and (C) a solvent. Preferably, the high viscosity bonding resin compound is 2,2-bis[4-(2-hydroxy-3-methacryloxypropoxy) phenyl] (Bis-GMA), 2,7,7,9,15-pentamethyl-4,13-dioxo-3,14-dioxa-5,12-diaza-hexadecane-1,16-diyl dimethacrylate (UDMA), or mlxtures thereof. Preferably. the second monomer is HEMA. Preferably, the photoinitiator comprises camphorquinone. Preferably, the solvent is selected from the group consisting of water and ethanol. Preferably, the solvent is selected from the group consisting of water and ethanol. Preferably, the bonding resin is an oligomer or prepolymer.

PREPARATION OF 6 FDMA

6FDMA is the reaction product of 1 mole of hexafluoroisopropylidine-2,2 bis(phthalic acid anhydride) and 2 moles of 2-hydroxyethyl methacrylate, identified hereafter as HEMA prepared as described in U.S. Pat. No. 5,338,773 at column 16, lines 9 through 27 incorporated herein by reference.

SYNTHESIS OF BTDMA

BTDMA is the reaction product of 1 mole of 3,3',4,4'-benzophenone tetracarboxylic acid dianhydride and 2 moles 2-hydroxyethyl methacrylate prepared as described in U.S. Pat. No. 5,338,773 at column 16, lines 30 through 46 incorporated herein by reference.

SYNTHESIS OF OEMA

OEMA is the reaction product of 1 mole 4,4'-oxydiphthalic anhydride (chemical name; 5,5'-oxybis-1,3-isobenzo furandione and 2 moles of HEMA, prepared as described in Lu et al, U.S. Pat. No. 5,338,773 at column 16, lines 53 through 63 incorporated herein by reference.

SYNTHESIS OF OPMA

OPMA is the reaction product of 1 mole oxydiphthalic anhydride and 2 moles of HPMA, prepared as described in Lu et al, U.S. Pat. No. 5,338,773 at column 16, lines 67–68 and column 17, lines 1 through 12 incorporated herein by reference.

PREPARATION OF STDMA

STDMA is the reaction product of 1 mole of 4,4'-sulfonyldiphthalic dianhydride (STDA) and 2 moles of HEMA STDMA is prepared in an excess of HEMA, prepared as described in U.S. Pat. No. 5,338,773 at column 17, lines 20 through 32 incorporated herein by reference.

PREPARATION OF OEMA IN TEGMA

OEMA is the reaction product of 1 mole of oxydiphthalic dianhydride (ODPA) and 2 moles HEMA.

In this example product is prepared in triethylene glycol dimethacrylate (TEGDMA) as a solvent, prepared as described in U.S. Pat. No. 5,338,773 at column 17, lines 36 through 59 incorporated herein by reference.

SYNTHESIS OF OEMA/GMA RESIN 31.0 grams (0.1 mole) 4,4-oxydiphthalic anhydride (ODPA), 11.4 grams of glutaric anhydride (0.1 mole), 39.0 grams of hydroxyethyl methacrylate (HEMA), (0.30 mole), and 0.05 grams of butylated hydroxytoluene are reacted at room temperature for 30 minutes followed by stirring at 110° C. for 2.0 hours to form a very viscous mixture of the adduct of ODPA and HEMA (OEMA) and an adduct of glutaric anhydride and HEMA (GMA).

SYNTHESIS OF 6FDMA/PMA RESIN ADDUCTS WITH HEMA 39.0 grams of HEMA, 0.06 g butylate hydroxytoluene, and 14.8 grams of phthalic anhydride are reacted at 100–110° C. for 60 minutes. Then 44.4 grams of hexafluoroisopropylidene-2,2-bis (phthalic acid anhydride) is added and stirred at between 120° and 130° C. for 4.0 hours to form a clear, slightly yellow resin mixture of 6FDMA and an adduct of phthalic anhydride and HEMA (PMA).

SYNTHESIS OF 6FDMA/GMA RESIN 39.0 grams (0.30 mole) hydroxyethylmethacrylate, 44.4 grams of hexafluorisopropylidene-2,2-bis (phthalic acid anhydride), 12.0 grams of glutaric anhydride and 0.06 grams of butylated hydroxytoluene are reacted at 100° C. for 4.0 hours to form a viscous slightly yellow clean resin, mixture of 6FDMA and an adduct of glutaric anhydride and HEMA (GMA).

PREPARATION OF POWDERS

Strontium aluminofluorosilicate glass powder used in Examples 13 and 14 is made by fusing aluminum oxide, silica, strontium fluoride aluminum fluoride, aluminum phosphate, and cryolite according to procedures disclosed in U.S. Pat. No. 4,814,362 to form particles which are milled to a mean particle size of 5.5 microns. It has the following analysis with all elements except fluorine being calculated as oxide of the element:
Composition of Strontium
  aluminofluorosilicate

| glass particles | Parts by weight |
|---|---|
| $Al_2O_3$ | 24.6 |
| $SiO_2$ | 32.1 |
| $Na_2O$ | 2.9 |
| SrO | 28.7 |
| F | 12.3 |
| $P_2O_5$ | 4.8 |

The barium aluminofluorosilicate glass particles used in Examples 13 and 14 are 7226 glass sold by Corning. It is preferably formed as disclosed in Danielson, U.S. Pat. No. 4,920,082.

Having generally described the invention, a more complete understanding can be obtained with reference to certain specific examples, which are included for purposes of illustration only. It should be understood that the invention is not limited to the specific details of the Examples.

EXAMPLE 1

A) Priming Adhesive Composition

A priming and adhesive polymerizable composition in accordance with the invention is formed by stirring 5.00 grams of OEMA; 10.00 grams of 7,7,9,63,65-hexamethyl-4,13,60,69-tetra-oxo-3,14,19,24,29,34,39,44,49,54,59,70-dodecanaoxa-5,12,61,68-tetra-azadoheptacontane-1,72-diyl-dimethacrylate, (also known as urethane dimethacrylate resin); 5.00 grams of 2,2,6-6-tetra-acryloxyloxymethyl-4,8-dioxa-9-oxo-11-undecyl phoshoric acid, also known as dipentaerythritol pentacrylate phosphoric acid ester (PENTA); 5.00 grams of 2-propenoic acid, 1-methyl-1,2-ethanediyl-bis (oxy-21-ethanediyl)ester, also known as triethylene glycol dimethacrylate (TEGMA); 0.01 grams of phenol, 2,6-bis-(1,1-dimethethyl-4-methyl), also known as butylated hydroxytoluene (BHT); 0.20 grams of bicyclo [2.2.1]heptane-2,3-dione 1,7,7-trimethyl, also known as camphorquinone; 0.60 grams of 4Ethyl dimethyl aminobenzoate (DMABE), and 79.19 grams of dimethyl ketone also known as dimethyl ketone.

B) Priming a Tooth Surface

A dental tooth surface of dentine and enamel is cleaned with pumice. Then the tooth surface is washed thoroughly with water spray and air-dried. Three drops of the priming adhesive composition, made by following the procedure of Example 1 Section A, are applied directly onto a brush. The priming adhesive composition is applied to the cleaned tooth Surface with the brush to thoroughly wet the exposed dentine and enamel surface. The surface is left undisturbed for 30 seconds. Excess solvent is removed by blowing with air from a dental syringe. The priming adhesive composition is then cured for 10 seconds to form a priming adhesive treated tooth.

C) Applying Restorative

Immediately Dyract restorative, sold by DENTSPLY International Inc. is placed over the cured priming adhesive. The restorative bonds to the treated tooth surface.

EXAMPLE 2

A) A primer adhesive composition is formed by stirring 81.56 grams of dimethyl ketone, 5.0 grams of triethyleneglycol dimethacrylate (TGD), 10.0 grams of OEMA, 10.0 grams of urethane diacrylate, 2.5 grams of PENTA, 0.20 grams of camphorquinone, 0.60 grams of DMABE, 0.05 grams of butylated hydroxytoluene (BHT).

B) The procedure of Example 1, sections B and C is followed except that the composition of Example 2 section A is used in place of the composition of Example 1, section A to form a restorative bonded to tooth dentin.

EXAMPLE 3

A) A primer adhesive composition is formed by stirring 76.65 grams of dimethyl ketone, 5.0 grams of TGD, 10.0 grams of urethane diacrylate, 7.5 grams of OEMA, 7.5 grams of PENTA, 0.20 grams of camphorquinone, 0.60 grams of DMABE, 0.05 grams of BHT.

B) The procedure of Example 1, sections B and C is followed except that the composition of Example 3 section A is used in place of the composition of Example 1, section A to form a restorative bonded to the tooth dentin.

EXAMPLE 4

A) A primer adhesive composition is formed by stirring 71.65 grams of dimethyl ketone, 5.0 grams of TGD, 10.0 grams of urethane diacrylate, 12.5 grams of OEMA, 12.5 grams of PENTA, 0.20 grams of camphorquinone, 0.60 grams of DMABE, 0.05 grams of BHT.

B) The procedure of Example 1, sections B and C is followed except that the composition of Example 4 section A is used in place of the composition of Example 1, section A to form a restorative bonded to the tooth dentin.

EXAMPLE 5

A) A primer adhesive composition is formed by stirring 81.65 grams of dimethyl ketone, 7.5 grams of TGD, 7.5 grams of urethane diacrylate, 2.5 grams of OEMA, 2.5 grams of PENTA, 0.20 grams of camphorquinone, 0.60 grams of DMABE, 0.05 grams of BHT.

B) The procedure of Example 1, sections B and C is followed except that the composition of Example 5 section A is used in place of the composition of Example 1, section A to form a restorative bonded to the tooth dentin.

EXAMPLE 6

A) A primer adhesive composition is formed by stirring 79.15 grams of dimethyl ketone, urethane diacrylate, 15.0 grams of urethane dimethacrylate, 5.0 grams of PENTA, 0.20 grams of camphorquinone, 0.60 grams of DMABE, 0.05 grams of BHT.

B) The procedure of Example 1, sections B and C is followed except that the composition of Example 6 section A is used in place of the composition of Example 1, section A to form a restorative bonded to the tooth dentin.

EXAMPLE 7

A) A primer adhesive composition is formed by stirring 80 grams of ethanol, 15 grams of TGD, 5 grams of OEMA, 5 grams of PENTA, 0.20 grams of camphorquinone, 0.60 grams of DMABE, 0.05 grams of BHT.

B) The procedure of Example 1, sections B and C is followed except that the composition of Example 7 section A is used in place of the composition of Example 1, section A to form a restorative bonded to the tooth dentin having a bond strength of 12.7 MPa.

EXAMPLE 8

A) A primer adhesive composition is formed by stirring 60 grams of ethanol, 35 grams of triethyleneglycol dimethacrylate (TGD), 5.0 grams of PENTA, 0.20 grams of camphorquinone, 0.60 grams of DMABE, 0.05 grams of BHT.

B) The procedure of Example 1, sections B and C is followed except that the composition of Example 8 section A is used in place of the composition of Example 1, section A to form a restorative bonded to the tooth dentin.

EXAMPLE 9

A) A primer adhesive composition is formed by stirring 80 grams of ethanol, 15 grams of tetrahydrofuran dimethacrylate (THFMA), 5 grams of OEMA, 5 grams of PENTA, 0.20 grams of camphorquinone, 0.60 grams of DMABE, 0.05 grams of BHT.

B) The procedure of Examples 1, sections B and C is followed except that the composition of Example 9 section A is used in place of the composition of Example 1, section A to form a restorative bonded to the tooth dentin.

EXAMPLE 10

A) A primer adhesive composition is formed by stirring 80 grams of dimethyl ketone, 5 grams of TGD, 10 grams of urethane diacrylate, 5 grams of OEMA, 5 grams of PENTA, 0.20 grams of camphorquinone, 0.60 grams of DMABE, 0.05 grams of BHT.

B) The procedure of Example 1, sections B and C is followed except that the composition of Example 10 section A is used in place of the composition of Example 1, section A to form a restorative bonded to the tooth dentin.

EXAMPLE 11

A tooth dentine is etched. A liquid composition is prepared by stirring 6 grams of OEMA, 6 grams of PENTA, 12 grams of TCB, 0.2 grams of CQ, 0.4 grams ethyl 4-dimethylaminobenzoate (DMABE), 0.05 grams of BHT and 87.35 grams of 95% ethanol. The liquid composition is applied onto the tooth by brushing. Then Prisma® APH™ restorative (sold by DENTSPLY International Inc.) is applied to the tooth and cured to obtain a bond.

For Example 11 shear bond strength is determined by treating extracted human teeth in 1% sodium hypochlorite for 18 to 24 hours, washing with water, and storing in distilled water in a refrigerator at about 4° C. until needed. The teeth are mechanically wet sanded with 120/320/600 grit carborundum paper until the dentin is exposed. Each tooth sample is then prepared by blotting dry exposed dentin with absorbent material, such as Kimwipe; etching dentin with 10% phosphoric acid for 15 seconds; rinsing with water for 15 seconds; and then blotting dry with absorbent material, such as Kimwipe. Two coats of adhesive composition are then applied to dentin with a brush for 30 seconds; dried with oil-free air for five seconds; curing for 20 seconds with a Max™Lite light curing unit. Prisma® APH™ restorative is placed in a cylindrical plastic matrix with a 3.68 mm inside diameter, set on the treated dentin and cured for 40 seconds. The specimens are stored in distilled water for approximately 24 hours at 37° C. Each specimen is mounted vertically in a plastic cylinder with self cure polymethyl methacrylate so that the dentin surface is parallel to the Instron needle; and then debonded on an Universal Instron with a crosshead speed of 5 mm/minute. The bond strength is then calculated in MPa.

EXAMPLE 12

One Component VLC Composition 30.10 grams of 6-FDMA/PMA resin formed by following the above procedure; 30.1 grams of PENTA, 2.50 grams of water; 65.10 grams of UDMA; 0.20 grams of camphorquinone; 0.60 grams of EDAB; 1.00 gram of 2-hydroxy-4-methoxybenzophenone (Uvinol M-40); and 0.50 grams of butylated hydroxytoluene are stirred to form an activated resin. 25.0 grams of the activated resin is mixed with 75.0 grams barium aluminofluorosilicate glass (60% silanted 40% unsilanated) to form a paste having a shelf stable polymerizable complex. The paste is cured by transmission thereinto of visible light from a The Max Lite™ polymerization unit sold by DENTSPLY International Inc to form polymeric material having a compressive strength of 29334 psi; a flexural strength of 72.1 MPa and a flexural modulus of 8939.6. MPa.

Synthesis of 6-FDMA/GMA Resin 3940 grams (0.30 mole) hydroxyethylmethacrylate, 44.4 grams of hexafluoroisopropylidne-2,2-bis (phthalic acid anhydride), 12.0 grams of glutaric anhydride and 0.06 grams of butylated hydroxytoluene are reacted at 100° C. for 4.0 hours to form a viscous slightly yellow clean resin, mixture of 6-FDMA and an adduct of glutaric anhydride and HEMA (GMA).

EXAMPLE 13

A one component VLC paste composition is formed by mixing 9.20 grams of 6-FDMA/GMA (formed by following the procedures of the immediately proceeding paragraph, 9.2 grams of PENTA, 0.80 grams of water; 15.0 grams of urethane dimethacrylate (2,7,7,9,15-pentamethy-4,13-dioxo-3,14-dioxa-5,12-diaza-hexadecane-1,16-diyl dimethyacrylate); 0.05 grams of camphorquinone; 0.30 grams of ethy-4-dimethylaminobenzoate (EDAB); 0.0125 grams of butylated hydroxytoluene; 0.075 grams of Uvinol MA-40; 37.5 silanated strontium aluminofluorosilicate glass powder and 37.5 grams of silanated barium aluminnofluorosilicate glass The paste is cured by transmission thereinto of visible light from The Max Lite (™) polymerization unit sold by DENTSPLY International Inc to form polymeric material having a flexural strength of 82 MPa; a flexural modulus of 10948; and compressive strength of 31954 psi.

EXAMPLE 14

10.75 grams of adduct of hexafluoroispropylidene-2, 2-bis(phthalic anhydride) and 2-hydroxyethyl methacrylate, 4.61 grams of 2-hydroxyethyl methacrylate, 7.2 grams of triethylene glycol dimethacrylate, and 0.98 grams of water are mixed with 0.048 grams of bicyclo(2,2,1)heptane-2, 3-ione 1,7,7-trimethyl, 0.144 grams of 4-ethyl dimethylaminobenzoate, 0.24 grams of methanone(2-Hydroxy-methoxyphenyl)phenyl, 10 grams of PENTA, and 0.024 grams of 2,6-bis(1,1-dimethethyl)-4-methyl phenol to form a polymerizable liquid. 37.24 grams of silanated strontium aluminofluorosilicate, 38.0 grams of barium aluminofluorosilicate glass, 0.76 grams of aerosil R-972 are formed into a power blend which is then mixed with the polymerizable liquid to form a one-component light curable dental adhesive paste composition which does not set within 6 months without polymerization initiation. The paste is cured by transmission thereinto of visible light from a The Max lite TM polymerization unit sold by DENTSPLY International Inc to form polymeric material.

EXAMPLE 15

Preparation of OEMA 155.1 gram (0.5 mole) of 4,4'-oxydiphthalic anhydride (ODPA), 143.4 gram (1.10 mole) of 2-hydroxyethylmethacrylate (HEMA), 12.2 gram (0.1 mole) of 4-dimethylamino pyridine (DMAP) and 400 mL of methylene chloride were added into the four necked flask equipped with mechanical stirrer, condenser, thermometer and additional funnel. After the mixture was stirred for 20 minutes, 101.2 gram (1.0 mole) of triethylamine dissolved in 100 mL methylene chloride was added dropwisely into the flask to keep the reaction temperature at 30–40° C. The obtained homogeneous solution was stirred for additional two hours. The reaction mixture was washed by 1 M HCl for three times and water for two times. After drying over anhydrous magnesium sulfate overnight, the solution was filtered and the solvent was removed by rotatory evaporation to yield 285.5 gram of viscous liquid. The material was characterized by IR and $^1$HNMR.

IR Disappearance of C=O stretching of anhydride group at ~1860 cm$^{-1}$ and ~1790 cm$^{-1}$. 1HNMR: 8.1–8.5 ppm (2H, s, —COOH), 7.0–8.1 ppm (6H, multiplet, aromatic region), 6.1 ppm (2H, s, vinyl protons trans to ester), 5.5 ppm (2H, s, vinyl protons cis to ester), 4.2–4.6 ppm (8H, mutiplet, methylene protons) and 1.9 ppm (6H, s, metyl protons of methacrylate group).

EXAMPLE 16

FORMULATION OF SELF-PRIMING METAL ADHESIVE 7.98 grams dipentaerythritol pentacrylate phosphoric acid ester (PETA); 8.78 grams 2,7,7,9,15-pentamethyl-4, 13-dioxo-3, 14-dioxa 5,12-diaza-hexadecane-1, 16diyldimetylate (UDMA); 3.33 grams 7, 7, 9 63, 63, 65-hexamethyl-4, 13, 60, 69-tetra-xo-3, 14, 19, 24, 29, 34, 39, 44, 49, 54, 59, 70-dodecanoxa-5, 12, 61, 68-tetra-aza-doheptacontane-1, 72-diyl-dimethacrylate resin; 5.04 grams a mixture of 1,1', 2,2' and 1,2'-bis-methacryloyloxy-ethyl-4,4'-oxydiphthalate (OEMA); 0.20 grams camphorquinone (CQ); 0.60 grams ethyl-4,N,N-dimethylaminobenzoate (EDAB); 0.10 grams butylated hydroxytoluene (BHT); 14.83 grams ethanol and 59.14 grams acetone are mixed at 23° C. for 30 minutes to form a Self-Priming Metal Adhesive.

EXAMPLE 17

FORMULATION OF SELF-PRIMING METAL ADHESIVE 7.98 grams dipentaerythritol pentacrylate phosphoric acid ester (PENTA)); 8.78 grams 2,7,7,9,15-pentamethyl-4, 13-dioxo-3, 14-dioxa 5,12-diaza-hexadecane-1, 16-diyl-dimethacrylate (UDMA); 3.33 grams 7, 7, 9 63, 63, 65-hexamethyl-4, 13, 60, 69-tetra-oxo-3, 14, 19, 24, 29, 34, 39, 44, 49, 54, 59, 70-dodecaneoxa-5, 12, 61, 68-tetra-aza-doheptacontane-1, 72-diyl-dimethacrylate resin; 5.04 grams mixture of 1,1', 2,2' and 1,2'-bis-methacryloyloxy-ethyl-4, 4'-oxydiphthalate (OEMA); 0.20 grams camphorquinone (CQ); 0.60 grams ethyl-4,N,N-dimethylaminobezoate (EDAB); 0.10 grams butylated hydroxytoluene (BHT) and 73.97 grams acetone are mixed at 23° C. for 30 minutes to form a Self-Priming Metal Adhesive.

BONDING STRENGTH TEST METHOD USING METAL AS SUBSTRATE FOR EXAMPLE 18–26

ISO 10477 test methods were used to measure the bonding strength of composites to precious metal alloys, non-precious metal alloys and other metal substrate by using compositions of present invention.

A) Substrate Preparation. The surface of metal substrate were treated as follows prior to application of the adhesive composition 1) metal surfaces were polished with #320 and #600 grit SiC papers sequentially. 2) The polished surfaces were air abraded with 110 μm fresh aluminum oxide, and then cleaned with a dry hard brush. B) Bonding to Dental Alloys. 1) Dispense primer/adhesive into a clean mixing well. 2) Apply a generous amount of the adhesive over the entire bonding surface. 3) The surface remained fully wet for 20 seconds, and then air dry for 10 seconds. 4) Light cure with curing unit. 5) Apply Licupast Opaquer two thin layer, For each layer, light cure with curing unit. 6) Incrementally place composites in two layers, and light cure with curing light apparatus. 7) Thermal cycle the bonding samples between 5° C. and 55° C. for 5000 cycles. 8) Test bonding strength using universal testing machine.

The following products are referred to in Examples 18–27 and Tables I–X: Targis Opaquer is an opaquer product of Ivoclar. HLC Bond is in adhesive product of Vita Zeta Artglass is an opaquer product of Heraeus Kulzer. Sinfony is a composite product of ESPE. LC-OD A3 is an opaquer product of DENTSPLY DeTrey GmbH. In Examples 18–27 and Tables I–X Sample Composite refers to a composite composition formed by mixing 3.52 percent by weight 2,2-Bis[4-(2-methacryloxyethoxy)phenyl]propane, 8.6 percent by weight 2,2'-[Ethanediylbis(oxy)]bisethyl-di-2-methyl-propenate, 10.45 percent by weight Cyclodi-2,2'-bis{4-(3-methacryloxy-2-(1,12-dioxa-2,11-dioxo-3,10-diazadodecane)propoxyl]phenyl}propane, 0.0345 percent by weight 1,7,7-Trimethylbicyclo[2,2,1]heptane-2, 3, dione and 0.115 percent by weight Ethyl-(4-N,N-dimethylamino) benzoate, 0.0058 percent by weight 2,6-bis(1,1-dimethylethyl)-4-methylphenol, 0.23 percent by weight (2-Hydroxy-methoxyphenyl)phenyl Methanone, 0.046 percent by weight Diethyl 2,5-dihydroxyterephthalate, 66.99 percent by weight Barium fluoro alumino borosilicate glass, 2.32 percent by weight Amorphous silica and 7.7 percent by weight polyacrylate powder, Then applying the composite composition to a tooth and light curing the composite composition to form Sample Composite.

EXAMPLE 18

Shear bond strength of composites to Wiron 99 nickel chromium alloy (Ni—Cr) non-precious metal using Self-Priming Metal Adhesive made by the following procedure of Example 17, and major commercial products are listed in the Table I.

TABLE I

Shear Bond Strength of Composites to Wiron 99

| Adhesive | Opaquer | Composite | Alloy | Curing Unit | SBS (MPa) |
|---|---|---|---|---|---|
| Self-Priming Metal Adhesive (Example 17) | LC-OD A3 | Sample Composite DA3 | Wiron 99 (Ni—Cr) | Liculite | 30.8 ± 4.6 |
| SeLf-Priming Metal Adhesive (Example 17) | LC-OD A3 | Sample Composite DA3 | Wiron 99 (Ni—Cr) | Triad 2000 | 24.3 ± 4.2 |
| Self-Priming Metal Adhesive (Example 17) | LC-OD A3 | Licupast Plus DC3 | Wiron 99 (Ni—Cr) | Triad 2000 | 20.6 ± 2.2 |
| Self-Priming Metal Adhesive (Example 17) | LC-OD A3 | Licupast Plus DC3 | Wiron 99 (Ni—Cr) | Liculite | 21.1 ± 3.1 |
| Targis Link | Targis Opaquer 4 | Targis D310 | Wiron 99 (Ni—Cr) | Targis Power | 17.2 ± 2.8 |
| HLC Bond | Opaquer A3 | VitaZeta DA3 | Wiron 99 (Ni—Cr) | Triad 2000 | 17.1 ± 4.6 |
| Siloc Pre/Bond | Artglass OA3 | Artglass DA3 | Wiron 99 (Ni—Cr) | Dentacolor XS | 16.3 ± 1.8 |
| ESPE-Sil | Sinfony OA3 | Sinfony DA3 | Wiron 99 (Ni—Cr) | ESPE/BETA | 12.4 ± 2.1 |

EXAMPLE 19

Shear bond strength of composites to precious metal Maingold SG using Self-Priming Metal Adhesive (formed by following the procedure of Example 17), and major commercial products were tested. The results were listed in the table II.

EXAMPLE 20

Shear bond strength of composites to Wironit (Co—Cr alloy) using Self-Priming Metal Composite Primer Adhesive (formed by following the procedure of Example 17), and major commercial products. The results were listed in the table III.

TABLE II

Shear Bond Strength of Composites to Maingold

| Adhesive | Opaquer | Composite | Alloy | Curing Unit | SBS (MPa) |
|---|---|---|---|---|---|
| Self-priming Metal Adhesive (Example 17) | LC-OD A3 | Sample Composite DA3 | Maingold SG | Triad 2000 | 22.5 ± 6.5 |
| Self-Priming Metal Adhesive (Example 17) | LC-OD A3 | Licupast Plus DC3 | Maingold SG | Triad 2000 | 14.9 ± 2.3 |
| Self-Priming Metal Adhesive (Example 17) | LC-OD A3 | Licupast Plus DC3 | Maingold SG | Liculite | 15.7 ± 2.7 |
| Targis Link | Opaquer 4 | Targis D310 | Maingold SG | Targis Power | 16.6 ± 3.1 |
| HLC Bond | Opaquer A3 | VitaZeta DA3 | Maingold SG | Triad 200 | 18.1 ± 4.2 |
| Siloc Pre/Bond | Artglass OA3 | Artglass DA3 | Maingold SG | Dentacolor XS | 12.5 ± 2.2 |
| ESPE-Sil | Sinfony OA3 | Sinfony DA3 | Maingold SG | ESPB/BETA | 11.4 ± 1.5 |

TABLE III

Shear Bond Strength of Composites to Wironit

| Adhesive | Opaquer | Composite | Alloy | Curing Unit | SBS (MPa) |
|---|---|---|---|---|---|
| Self-Priming Metal Adhesive (Example 17) | LC-OD A3 | Sample Composite | Wironit (Co—Cr) | Prismetics Lite II | 27.6 ± 6.9 |
| Self Priming Metal Adhesive (Example 17) | LC-OD A3 | Sample Composite | Wironit (Co—Cr) | Liculite | 32.0 ± 4.4 |
| Self-Priming Metal Adhesive (Example 17) | LC-OD A3 | Sample Composite | Wironit (Co—Cr) | Triad 2000 | 25.8 ± 4.6 |
| Self-Priming Metal Adhesive (Example 17) | LC-OD A3 | Sample Composite | Wironit (Co—Cr) | Spectrum Lite | 29.2 ± 3.6 |
| Targis Link | Opaquer 4 | Targis D310 | Wironit (Co—Cr) | Targis Power | 15.6 ± 3.1 |

EXAMPLE 21

Shear bond strength of composites to Titan using Self-Priming Metal Composite Primer Adhesive (formed by following the procedure of Example 17), and major commercial products were tested. The results were listed in the table IV.

TABLE IV

Shear Bond Strength of Composites to Titan

| Adhesive | Opaquer | Composite | Alloy | Curing Unit | SBS (MPa) |
|---|---|---|---|---|---|
| Self-Priming Metal Adhesive (Example 17) | LC-OD A3 | Sample Composite | Titan | Prismetics Lite II | 39.3 ± 3.7 |
| Self-Priming Metal Adhesive (Example 17) | LC-OD A3 | Sample Composite | Titan | Liculite | 33.1 ± 4.8 |
| Self-Priming Metal Adhesive (Example 17) | LC-OD A3 | Sample Composite | Titan | Triad 2000 | 33.3 ± 4.6 |
| Self-Priming Metal Adhesive (Example 17) | LC-OD A3 | Sample Composite | Titan | Spectrum Lite | 30.8 ± 2.6 |
| Targis Link | Opaquer 4 | Targis D310 | Titan | Targis Power | 15.7 ± 2.6 |

EXAMPLE 22

Shear bond strength of composites to Bego PAL300 using the Adhesive (formed by following the procedure of Example 17), were tested. The results were listed in the table V.

TABLE V

Shear Bond Strength of Composites to Bego PAL300

| Adhesive | Opaquer | Composite | Alloy | Curing Unit | SBS (MPa) |
|---|---|---|---|---|---|
| Self-Priming Metal Adhesive (Example 17) | LC-OD A3 | Sample Composite | Bego PAL300 | Spectrum Lite | 21.2 ± 3.2 |
| Self-priming Metal Adhesive (Example 17) | LC-OD A3 | Sample Composite | Bego PAL300 | Liculite | 17.2 ± 3.8 |

TABLE V-continued

Shear Bond Strength of Composites to Bego PAL300

| Adhesive | Opaquer | Composite | Alloy | Curing Unit | SBS (MPa) |
|---|---|---|---|---|---|
| Self-Priming Metal Adhesive (Example 17) | LC-OD A3 | Sample Composite | Bego PAL300 | Triad 2000 | 16.3 ± 4.1 |
| Self Priming Metal Adhesive (Example 17) | LC-CD A3 | Licupast Plus DC3 | Bego PAL300 | Triad 2000 | 14.1 ± 0.7 |
| Self-Priming Metal Adhesive (Example 17) | LC-OD A3 | Licupast Plus DC3 | Bego PAL300 | Liculite | 12.7 ± 1.9 |

EXAMPLE 23

Shear bond strength of composites to Bego Ger G using Composite Primer Adhesive (formed by following the procedure of Example 17), were teste. The results were listed in the table VI.

TABLE VL

Shear Bond strength of Composites to Bego Ger G

| Adhesive | Opaquer | Composite | Alloy | Curing Unit | SBS (MPa) |
|---|---|---|---|---|---|
| Self-Priming Metal Adhesive (Example 17) | LC-OD A3 | Sample Composite | Bego Cer G | Spectrum Lite | 17.2 ± 4.0 |
| Self-Priming Metal Adhesive (Example 17) | LC-OD A3 | Sample Composite | Bergo Cer G | Liculite | 12.2 ± 1.9 |
| Self-Priming Metal Adhesive (Example 17) | LC-OD A3 | Sample Composite | Bego Cer G | Triad 2000 | 13.8 ± 3.2 |
| Self-Priming Metal Adhesive (Example 17) | LC-QD A3 | Licupast Plus DC3 | Bego Cer G | Triad 2000 | 10.6 ± 1.6 |
| Self-Priming Metal Adhesive (Example 17) | LC-OD A3 | Licupast Plus DC3 | Bego Cer G | Liculite | 10.7 ± 1.5 |

EXAMPLE 24

Shear bond strength of composites to AuroLloyd KF using Self-Priming Metal Adhesion Composite Primer Adhesive (formed by following the procedure of Example 16), were tested. The results were listed in the table VII.

TABLE VII

Shear Bond Strength of Composites to AuroLloyd KF

| Adhesive | Opaquer | Composite | Alloy | Curing Unit | SBS (MPa) |
|---|---|---|---|---|---|
| Self-Priming Metal Adhesive (Example 17) | LC-OD A3 | Sample Composite | AuroLloyd KF | Spectrum Lite | 15.6 ± 5.9 |
| Self-Priming Metal Adhesive (Example 17) | LC-OD A3 | Sample Composite | AuroLloyd KF | Liculite | 14.2 ± 3.3 |
| Self-Priming Metal Adhesive (Example 17) | LC-OD A3 | Sample Composite | AuroLloyd KF | Triad 2000 | 13.4 ± 0.9 |
| Self-Priming Metal Adhesive (Example 17) | LC-OD A3 | Licupast Plus DC3 | AuroLloyd KF | Triad 2000 | 13.9 ± 1.7 |

TABLE VII-continued

Shear Bond Strength of Composites to AuroLloyd KF

| Adhesive | Opaquer | Composite | Alloy | Curing Unit | SBS (MPa) |
|---|---|---|---|---|---|
| Self-Priming Metal Adhesive (Example 17) | LC-OD A3 | Licupast Plus DC3 | AuroLloyd KF | Liculite | 11.4 ± 1.6 |

EXAMPLE 25

Shear bond strength of composites to Bioplatin Lloyd using Composite Primer Adhesive (formed by following the procedure of Example 16), were tested. The results were listed in the table VIII.

TABLE VIII

Shear Bond Strength of Composites to Bioplatin Lloyd

| Adhesive | Opaquer | Composite | Alloy | Curing Unit | SBS (MPa) |
|---|---|---|---|---|---|
| Self-Priming Metal Adhesive (Example 17) | LC-OD A3 | Sample Composite | BioPlatin Lloyd | Spectrum Lite | 13.4 ± 3.1 |
| Self-Priming Metal Adhesive (Example 17) | LC-OD A3 | Sample Composite | BioPlatin Lloyd | Liculite | 10.8 ± 1.5 |
| Self-Priming Metal Adhesive (Example 17) | LC-OD A3 | Sample Composite | BioPlatin Lloyd | Triad 2000 | 14.8 ± 4.1 |
| Self-Priming Metal Adhesive (Example 17) | LC-OD A3 | Licupast Plus DC3 | BioPlatin Lloyd | Triad 2000 | 10.5 ± 1.4 |
| Self-Priming Metal Adhesive (Example 17) | LC-OD A3 | Licupast Plus DC3 | BioPlatin Lloyd | Liculite | 12.6 ± 1.8 |

EXAMPLE 26

Shear bond strength of composites to Biopontostar using Self-Priming Metal Adhesive Composite Primer Adhesive (formed by following the procedure of Example 17) were tested. The results were listed in the table IX.

TABLE IX

Shear Bond Strength of Composites to Biopontostar

| Adhesive | Opaquer | Composite | Alloy | Curing Unit | SBS (MPa) |
|---|---|---|---|---|---|
| Self-Priming Metal Adhesive (Example 17) | LC-OD A3 | Sample Composite | BioPontostar | Liculite | 13.5 ± 3.1 |
| Self-Priming Metal Adhesive (Example 17) | LC-OD A3 | Sample Composite | BioPontostar | Triad 2000 | 13.3 ± 4.4 |

TABLE X

Composition of Dental Alloys used in Example 18–26

| Alloy | Percent by weight | | | | | | | | | Manufacturer |
|---|---|---|---|---|---|---|---|---|---|---|
| | Au | Pt | Pd | Ag | Cu | Ga | Sn | Zn | In | |
| Maingold | 71.0 | 2.0 | 2.0 | 12.3 | 12.2 | — | — | <2 | — | Heraeus |

TABLE X-continued

Composition of Dental Alloys used in Example 18–26

| Alloy | Percent by weight | | | | | | | | | Manufacturer |
|---|---|---|---|---|---|---|---|---|---|---|
| BegoCer G | 51.5 | — | 38.4 | — | — | 1.3 | — | — | 8.7 | Bego |
| BegoPal 300 | 6.0 | — | 75.4 | 6.2 | — | 6.0 | — | — | 6.3 | Bego |
| AuroLioyd KF | 55.0 | — | 10.0 | 29.2 | — | — | 1.0 | 1.2 | 3.5 | Bego |
| Bio Platin Lioyd | 75.1 | 7.8 | — | 14.8 | — | — | — | 1.8 | — | Bego |
| | Au | Pt | Rh | Mn | Ta | Ga | Sn | Zn | In | |
| Bio Pontostar | 87.0 | 10.6 | 0.2 | 0.2 | 0.2 | — | — | 1.5 | 0.3 | Bego |
| | Ni | Co | Cr | Mo | Si | Nb | Mn | Fe | Ce | |
| Wiron 99 | 65.0 | — | 22.5 | 9.5 | 1.0 | 1.0 | — | 0.5 | 0.5 | Bego |
| Wironit | — | 64.0 | 28.6 | 5.0 | 1.0 | — | 1.0 | — | — | Bego |

EXAMPLE 27

Bonding Strength Test Method Using Ceramic as Substrate

Caulk compressive shear bond strength test methods were used to measure the bonding strengths of composites to ceramic by using compositions of present invention (Example 17).
A). Substrate Preparation. Prior to application of the adhesive composition, the surfaces of ceramic substrate were treated as follows. 1). Ceramics surfaces were polished with #320 and #600 grit SiC papers sequentially. 2). The polished surfaces were air abraded with 50 μm fresh aluminum oxide, and then cleaned with deionized water and dried in the air. 3). Apply Silane Coupling Agent (Caulk/DENTSPLY) in two thin layers.

Bonding to Dental Ceramic. 1). Dispense primer/adhesive into a clean mixing well. 2). Apply a generous amount of the adhesive over the entire ceramic bonding surface. 3). The surface remained fully wet for 20 seconds, and then air dry for 10 seconds. 4). Light cure with curing unit. 6). Place filled straw with composite, and light cure with Spectrum curing light for 20 seconds. 7). Test bonding strength using universal testing machine.

The obtained Shear Bond Strength of composite to ceramic was 22.13 MPa (mean).

EXAMPLE 28

SYNTHESIS OF OEMA/GMA RESIN 31.0 grams (0.1 mole) 4,4-oxydiphthalic anhydride (ODPA), 11.4 grams of glutaric anhydride (0.1 mole), 39.0 grams of hydroxyethyl methacrylate (HEMA), (0.30 mole), and 0.05 grams of butylated hydroxytoluene are reacted at room temperature for 30 minutes followed by stirring at 110° C. for 2.0 hours to form a very viscous mixture of the adduct of ODPA and HEMA (OEMA) and an adduct of glutaric anhydride and HEMA (GMA).

EXAMPLE 29

ONE COMPONENT VLC COMPOSITION 30.50 grams of OEMA/GMA resin are formed as described in Example 28; 2.50 grams of water; 65.10 grams of 2,7,7,9, 15-pentamethyl-4,13-dioxo-3, 14-dioxa-5,12-diaza-hexadecane-1,16-diyl dimethacrylate (UDMA); 0.20 grams of camphorquinone; 0.60 grams of EDAB; 1.00 gram of 2-hydroxy4-methoxybenzophenone (Uvinol M-40 sold by BASF) and 0.50 grams of butylated hydroxytoluene (BHT) are stirred to form an activated resin. 5.0 grams of the activated resin is mixed with 15.0 grams of barium alumi-nofluorosilicate glass powder (67% silanated and 33% unsilanated) to form a paste having a shelf stable polymerizable complex which does not set within 6 months in the absence of polymerization initiation. The paste is cured by transmission thereinto of visible light from The Max lite TM polymerization unit sold by Dentsply International Inc to form a polymeric material having a compressive strength of 31533 psi.

EXAMPLE 30

6FDMA is the reaction product of 1 mole of hexafluoroisopropylidine-2,2 bis(phthalic acid anhydride) and 2 moles of 2-hydroxyethyl methacrylate, identified herein as HEMA.

13.3 grams(0.03 moles)hexafluoroisopropylidine-2,2bis (phthalic acid anhydride) and 12.6 grams (0.097 moles) of HEMA and 0.0006 grams of butylated hydroxytoluene are heated in a 100 ml round bottom flask equipped with a thermometer and a water cooled condenser with a drying tube. The mixture is stirred while heating slowly to 100° C. Thereafter the temperature is maintained at 110° C. for one hour, then 16 hours overnight at 50° C., then a further 3.5 hours at 110° C. The solution is cooled to room temperature. The solution contains 70% by weight of 6FDMA and 30% by weight of HEMA and has IR absorptions at: 2500–3500 $cm^{-1}$, broad; 1715 $cm^{-1}$ broad; 1630 $cm^{-1}$; 1130–1450 $cm^{-1}$ broad; 1170 $cm^{-1}$; 950$cm^{-1}$; and 800 $cm^{-1}$ multiplet.

EXAMPLE 30A

SYNTHESIS OF OEMA

OEMA is the reaction product of 1 mole 4,41' oxydiphthalic anhydride (chemical name: 5,5'-oxybis-1,3-isobenzo furadione) and 2 moles of HEMA.

35.6 grams (0.115 moles) of 4,4'-oxydiphthalic anhydride and 58.0 grams (0.045 moles) of EMA are reacted at 110° C. for 4 hours to provide a clear oily solution of OEMA in an excess of HEMA, having a viscosity of 5250 cps, and IR absorptions at 2700–3550 $cm^{-1}$ very broad; 1715 $cm^{-1}$ broad; 163 $cm^{-1}$, 1590 $cm^{-1}$; 1570 $cm^{-1}$; 1450 $cm^{-1}$; 1400 $cm^{-1}$; 1360 $cm^{-1}$; 1100–1330 $cm^{-1}$; 1165 $cm^{-1}$; 940 $cm^{-1}$; 810 $cm^{-1}$, and 785 $cm^{-1}$. This solution contains 70% by weight OEMA and 30% by weight of

EXAMPLE 31

A one component VLC composition is formed by stirring 10.75 grams of 6-FDMA (formed by following the procedure of Example 30), 4.61 grams of HEMA, 72 grams of TEGDMA, 0.98 grams of distilled water, 0.048 grams of camphorquinone, 0.144 grams of EDAB, 0.24 grams of Uvinol M-40 and 0.024 grams of BHT at room temperature to form a homogeneous activated resin. 2.4 grams of the activated resin is mixed with 7.6 grams of a powder blend of 99 grams of barium aluminofluorosilicate glass, 1 gram of Aerosil R-972 to make a stable paste. The paste is cured to form a polymeric adhesive having a compressive strength of 2.25 MPa, a bond strength to dentin of 1673 psi and a fluoride release shown in Table XI.

EXAMPLE 32

One component VLC sealant is formed by mixing 25.24 grams of OEMA, (formed by following the procedure of Example 30A)12.5 grams TEUDMA, 2.0 grams of distilled water, 0.04 grams of camphorquinone, 0.2 grams EDAB and 0.016 grams BHT to an homogeneous activated resin. 40 grams of barium aluminofluorosilicate glass is added to the resin to form a stable one component VLC sealant having which upon exposure to visible light forms a polymeric material having a compressive strength of 25521 psi, flexural strength 42 MPa, flexural modulus of 4071 MP and releases fluoride as shown in Table 3.

EXAMPLE 33

One component VLC sealant is formed by stirring 30.93 grams 6-FDMA formed by following the procedure of Example 30, 1.93 grams distilled water, 14.98 grams TEGDMA, 0.05 grams of camphorquinone, 0.24 grams EDAB and 0.025 grams BHT to form an activated resin, then add 51 grams barium aluminofluorosilicate glass and 0.77 grams aerosil R-972. The mixture is mixed to form a stable one component sealant which upon curing by exposure to visible light forms a polymeric material having a compressive strength of 31552 psi, dimetrial tensile strength of 5085 psi, flexural strength 74 MPa, flexural modulus of 3722 MPa, and a bond strength to enamel of 1160 psi.

The staric fluoride release for samples of products from Examples 31, 32, and 33 are shown in Table XI.

TABLE XI

STATIC RELEASE OF FLUORIDE IN MICROGRAMS OF FLUORIDE PER GRAM OF SAMPLE

| Week | Polymeric Product of Example 31 | Polymeric Product of Example 32 | Polymeric Product of Example 33 |
| --- | --- | --- | --- |
| 1 | 857.5 | 509.6 | 479.4 |
| 2 | 720.3 | 296.3 | 433.0 |
| 3 | 545.3 | 296.3 | 376.9 |
| 4 | 458.6 | 374.2 | 327.4 |
| 6 | 373.3 | 283.6 | 311.9 |
| 7 | 337.4 | 299.6 | 279.5 |
| 8 | 282.9 | 265.4 | 146.1 |
| 9 | 268.7 | 261.8 | 146.1 |
| 10 | 239.7 | 247.3 | 146.1 |
| 11 |  | 232.0 | 226.8 |
| 12 |  | 200.8 | 201.2 |

Polymerizable Salt Formation:

1.0 grams $Ca(OH)_2$, and a solution of 0.95 grams 6FDMA, 0.27 grams HEMA and 0.08 grams water are mixed. The IR spectrum of the mixture is measured immediately and shows neutralization of the acid and a broad IR absorption at 1390 $cm^{-1}$ and 1580 $cm^{-1}$, indicating sat formation.

1.0 grams of $Al_2O_3$, a solution of 0.65 grams 6FDMA, 0.27 grams HEMA and 0.08 grams of water are mixed. The IR spectrum of the mixture indicates salt formation by absorption at 1390 $cm^{-1}$ and 1580 $cm^{-1}$.

EXAMPLE 34

A resin mixture of 6 grams of an adduct of succinic anhydride and glycerol dimethacrylate (SGMA), 1.2 grams of dipentaeryothritol pentaacrylate phosphate (DPEPAP), prepared as described in U.S. Pat. No. 4,514,342, 2.4 grams of 2,2-bis[4-(2-hydroxy-3-methacryloxypropoxy)phenyl], (Bis-GMA), 0.573 grams of water, 0.02 grams of camphorquinone, 0.049 grams of EDAB and 0.01 grams of butylated hydroxytoluene (BHT) is mixed in a 50 ml plastic beaker to form a homogeneous liquid. Then, 31 grams of strontium aluminofluorosilicate glass powder is added and mixed to form a uniform paste. The paste is cured by transmission thereinto of visible light from a. The Max lite TM polymerization unit sold by DENTSPLY International Inc to form a polymeric material having static fluoride release shown in Table XII.

TABLE XII

| WEEKS | ppm | µg | µg/gram | Cum. µg/gram |
| --- | --- | --- | --- | --- |
| 1 | 7.5400 | 82.94 | 93.37 | 93.37 |
| 2 | 4.0050 | 44.06 | 49.59 | 142.96 |
| 3 | 3.4850 | 38.34 | 43.16 | 186.12 |
| 4 | 2.7900 | 30.69 | 84.44 | 220.67 |
| 5 | 2.2700 | 24.97 | 28.11 | 248.78 |
| 6 | 2.0800 | 22.88 | 25.76 | 274.54 |
| 7 | 1.9300 | 21.23 | 23.90 | 298.44 |
| 8 | 1.9150 | 21.07 | 23.71 | 322.15 |
| 9 | 1.6450 | 18.10 | 20.37 | 342.52 |
| 10 | 1.1450 | 12.60 | 14.18 | 356.70 |
| 11 | 1.2500 | 13.75 | 15.48 | 372.18 |
| 12 | 1.1480 | 12.53 | 14.22 | 386.39 |
| 13 | 1.0325 | 11.36 | 12.79 | 399.18 |
| 14 | 1.0325 | 11.36 | 12.79 | 411.96 |

It should be understood that while the present invention has been described in considerable detail with respect to certain specific embodiments thereof, it should not be considered limited to such embodiments but may be used in other ways without departure from the invention and the scope of the appended claims.

What is claimed is:

1. A dental composition, comprising:
   an amount of volatile organic solvent effective to form a solution comprising, at least 15 percent by weight of one or more polymerizable acrylate compounds and an effective amount of a photoinitiator, at least a portion of said polymerizable compounds are phosphorous containing multifunctional polymerizable compounds having at least three acrylate moieties, and a portion of said polymerizable compounds are aryl compounds, said polymerizable compounds being substantially soluble in said solvent.

2. The composition of claim 1 wherein said polymerizable composition is adapted to form a polymeric material which adheres to metal and metal alloy comprising at least 15 percent by weight of at least one metal selected from a group consisting of Au, Pt, Pd and Ag with a bond strength of at least 10 Mpa and said composition comprises at least 2 percent by weight of said multifunctional polymerizable compounds, said bond strength is at least 20.

3. The composition of claim 1 wherein said composition comprises at least 2.5 percent by weight of said multifunctional polymerizable compounds.

4. The composition of claim 1 wherein said composition comprises at least 3 percent by weight of said multifunctional polymerizable compounds.

5. The composition of claim 1 wherein said composition comprises at least 3.5 percent by weight of said multifunctional polymerizable compounds.

6. The composition of claim 1 wherein said composition comprises at least 4 percent by weight of said multifunctional polymerizable compounds.

7. The composition of claim 1 wherein said composition comprises at least 5 percent by weight of said multifunctional polymerizable compounds.

8. The composition of claim 1 wherein said composition comprises at least 6 percent by weight of said multifunctional polymerizable compounds.

9. The composition of claim 1 wherein said composition comprises at least 7 percent by weight of said multifunctional polymerizable compounds.

10. The composition of claim 1 wherein said solvent is dimethyl ketone or methyl ethyl ketone.

11. The composition of claim 1 wherein said composition comprises at least 70 percent by weight of said solvent.

12. The composition of claim 2 wherein at least a portion of said multifunctional polymerizable compounds are phosphate esters.

13. The composition of claim 2 wherein at least a portion of said multifunctional compounds have a chemical structure within the scope of the general formula:

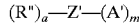

wherein each R' independently is an acrylate containing moiety,

Z' is an organic moiety, each A' independently is an acid or acid ester, n is an integer greater than 2, m is an integer of 1 or more.

14. The composition of claim 4 wherein said solvent is dimethyl ketone.

15. The composition of claim 1 wherein at least a portion of said polymerizable compounds are acids and said acids comprise at least 2 percent by weight of said composition.

16. The composition of claim 15 wherein said composition further comprises a polymerizable compound having at least two acrylate moieties and a gram molecular weight greater than 200, said polymerizable compound being adapted to form an elastomer when polymerized.

17. The composition of claim 15 further comprising carboxylic acids.

18. The composition of claim 1 wherein at least a portion of said polymerizable compounds are acid esters.

19. The composition of claim 1 wherein said polymerizable aryl compound is a compound within general formula

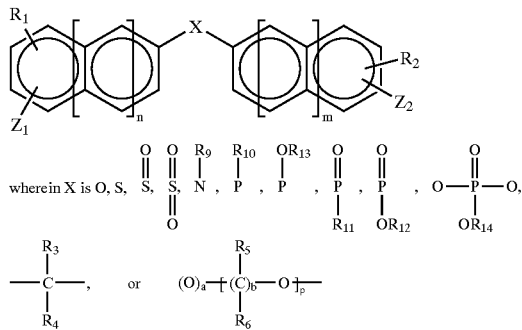

$R_1$ and $R_2$ each independently is a polymerizable unsaturated moiety having from 2 to 13 carbon atoms, $R_3$, $R_4$, $R_5$, and $R_6$ each independently is hydrogen, halogen, alkyl of from 1 to 10 carbon atoms or halogenated alkyl of from 1 to 10 carbon atoms, $R_9$, $R_{10}$, $R_{11}$, $R_{12}$, $R_{13}$ and $R_{14}$ each independently is hydrogen, alkyl having from 1 to 10 carbon atoms or aryl having from 6 to 10 carbon atoms, $Z_1$, and $Z_2$ each independently is a moiety including an acid group or a reactive acid derivative, a, m and n each independently is 0 or 1, b, and p each independently is an integer from 1 to 10; and 1 is a integer from 1 to 3.

20. The composition of claim 19 further comprising solvent.

21. The composition of claim 20 wherein said solvent comprises ethanol or water.

22. The composition of claim 20 wherein said compound within the general formula is the reaction product of 1 mole of 4,4' oxydiphthalic anhydride and 2 moles of 2-hydroxyethyl methacrylate (OEMA).

23. The composition of claim 19 wherein said compound containing phosphorous is dipentaeryøthritol pentaacrylate phosphate (DPEPAP).

24. The composition of claim 19 wherein said compound containing phosphorous is a penta acrylate.

25. The composition of claim 19 wherein said compound containing phosphorous is a phosphate.

26. The composition of claim 19 in the composition further comprising a diluent comonomer.

27. The composition of claim 19 wherein n and m are zero.

28. The composition of claim 19 wherein X is oxygen or

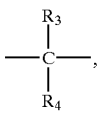

wherein $R_3$ and $R_4$ are fluorinated methyl moieties.

29. A dental polymeric material formed from a polymerizable composition, comprising:

an amount of volatile organic solvent effective to form a solution comprising at least 15percent by weight of one or more polymerizable acrylate compounds and an effective amount of a photoinitiator, at least a portion of said polymerizable compounds being phosphorous containing multifunctional polymerizable compounds having at least three acrylate moieties, and a portion of said polymerizable compounds being aryl compounds, said polymerizable compounds being substantially soluble in said solvent, said polymerizable composition being formed into a polymeric material which adheres to metal and metal alloy comprising at least 15 percent by weight of at least one metal selected from a group consisting of Au, Pt, Pd and Ag with a bond strength of at least 10 MPa.

30. The composition of claim 29 wherein said composition comprises at least 2 percent by weight of said multifunctional polymerizable compounds, said bond strength is at least 20.

31. The composition of claim 29 wherein said composition comprises at least 2.5 percent by weight of said multifunctional polymerizable compounds.

32. The composition of claim 29 wherein said composition comprises at least 3 percent by weight of said multifunctional polymerizable compounds.

33. The composition of claim 29 wherein said composition comprises at least 3.5 percent by weight of said multifunctional polymerizable compounds.

34. The composition of claim 29 wherein said composition comprises at least 4 percent by weight of said multifunctional polymerizable compounds.

35. The composition of claim 29 wherein said composition comprises at least 5 percent by weight of said multifunctional polymerizable compounds.

36. The composition of claim 29 wherein said composition comprises at least 6 percent by weight of said multifunctional polymerizable compounds.

37. The composition of claim 29 wherein said composition comprises at least 7 percent by weight of said multifunctional polymerizable compounds.

38. The composition of claim 29 wherein said solvent is dimethyl ketone or methyl ethyl ketone.

39. The composition of claim 29 wherein said composition comprises at least 70 percent by weight of said solvent.

40. The composition of claim 30 wherein at least a portion of said multifunctional polymerizable compounds are phosphate esters.

41. The composition of claim 30 wherein at least a portion of said multifunctional compounds have a chemical structure within the scope of the general formula:

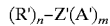

wherein each R' independently is an acrylate containing moiety,

Z' is an organic moiety, each A' independently is an acid or acid ester, n is an integer greater than 2, m is an integer of 1 or more.

42. The composition of claim 32 wherein said solvent is dimethyl ketone.

43. The composition of claim 29 wherein at least a portion of said polymerizable compounds are acids and said acids comprise at least 2 percent by weight of said composition.

44. The composition of claim 43 wherein said composition further comprises a polymerizable compound having at least two acrylate moieties and a gram molecular weight greater than 200, said polymerizable compound being adapted to form an elastomer when polymerized.

45. The composition of claim 40 further comprising carboxylic acids.

46. The composition of claim 29 wherein at least a portion of said polymerizable compounds are acid esters.

47. A polymeric material formed from a polymerizable composition for treating dental metal, comprising:
   a first portion of a liquid composition for applying to a dental metal surface, said liquid composition comprising an amount of volatile organic solvent effective to form a solution comprising at least 15 percent by weight of one or more polymerizable acrylate compounds and an effective amount of a photoinitiator, at least a portion of said polymerizable compounds are phosphorous containing multifunctional polymerizable compounds having at least three acrylate moieties, a portion of said polymerizable compounds being aryl compounds, said polymerizable compound being substantially soluble in said solvent, said composition being formed into a polymeric material which adheres to metal.

48. The composition of claim 47 further comprising a second portion of said liquid composition applied to said primed metal surface,
   said polymerizable compound in said second portion of said liquid priming adhesive composition being adapted to be cured to form a conditioned metal surface.

49. The composition of claim 47 further comprising a polymerizable restorative composition applied to said conditioned metal surface.

50. The composition of claim 49 wherein said polymerizable restorative composition is cured forming a polymeric restorative bonded to said metal with a bond strength at least 20 MPa.

51. The composition of claim 47 wherein said composition comprises at least 3 percent by weight of said multifunctional polymerizable compounds.

52. The composition of claim 47 wherein said composition comprises at least 5 percent by weight of said multifunctional polymerizable compounds.

53. The composition of claim 47 wherein at least a portion of said multifunctional compounds have a chemical structure within the scope of the general formula:

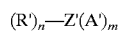

wherein each R' independently is an acrylate containing moiety,

Z' is an organic moiety, each A' independently is an acid or acid ester, n is an integer greater than 2, m is an integer of 1 or more.

54. The composition of claim 47 wherein at least a portion of said multifunctional compounds have a chemical structure within the scope of the general formula:

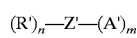

wherein each R' independently is an acrylate containing moiety,

Z' is an organic moiety, each A' independently is an acid or acid ester, n is an integer greater than 2, m is an integer of 1 or more.

55. A dental composition, comprising:
   an amount of volatile organic solvent effective to form a solution comprising one or more polymerizable acrylate compounds and an effective amount of a photoinitiator, at least a portion of said polymerizable compounds are phosphorous containing multifunctional polymerizable compounds having at least three acrylate moieties, and a portion of said polymerizable compounds are aryl compounds, said polymerizable compounds being substantially soluble in said solvent.

56. The composition of claim 55 wherein at least a portion of said polymerizable compounds are polymerizable compounds having at least one acid moiety and said polymerizable compounds having at least one acid moiety comprise at least 2 percent by weight of said composition.

57. A dental composition, comprising:
   an amount of volatile organic solvent effective to form a solution comprising one or more polymerizable acrylate compounds and an effective amount of a photoinitiator, at least a portion of said polymerizable compounds are phosphorous containing multifunctional polymerizable compounds having at least three acrylate moieties and a portion of said polymerizable compounds are aryl compounds having at least one carboxylic acid group and at least one polymerizable group, said polymerizable compounds being substantially soluble in said solvent.

58. The composition of claim 57 wherein said composition comprises at least 2 percent by weight of said multifunctional polymerizable compounds and said polymerizable composition being adapted to form a polymeric material which adheres to metal with a bond strength of at least 10 Mpa.

59. The composition of claim 56 wherein said composition comprises at least 2.5 percent by weight of said multifunctional polymerizable compounds.

60. The composition of claim 57 wherein at least a portion of said multifunctional compounds have a chemical structure within the scope of the general formula:

$(R')_n—Z'—(A')_m$ wherein each R' independently is an acrylate containing moiety, Z' is an organic moiety, each A' independently is an acid or acid ester, n is an integer greater than 2, m is an integer of 1 or more.

61. The composition of claim 57 wherein said multifunctional polymerizable compounds comprise dipentaerythritol pentacrylate phosphoric acid ester (PENTA) and said aryl compounds comprise a compound within general formula

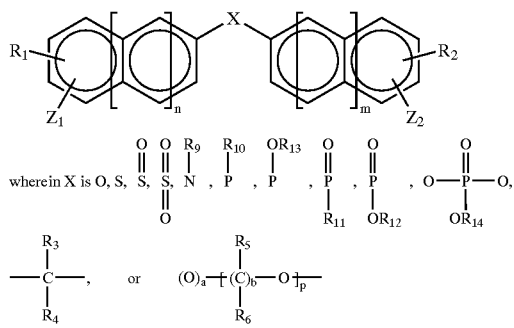

wherein X is O, S, $\begin{matrix} O \\ \| \\ S \\ \| \\ O \end{matrix}$, $\begin{matrix} O \\ \| \\ S \\ \| \\ O \end{matrix}$, $\begin{matrix} R_9 \\ | \\ N \end{matrix}$, $\begin{matrix} R_{10} \\ | \\ P \\ | \\ R_{11} \end{matrix}$, $\begin{matrix} OR_{13} \\ | \\ P \\ | \\ OR_{12} \end{matrix}$, $\begin{matrix} O \\ \| \\ P \\ | \\ OR_{14} \end{matrix}$, $\begin{matrix} O \\ \| \\ O—P—O \\ \| \\ O \end{matrix}$, $\begin{matrix} R_3 \\ | \\ —C— \\ | \\ R_4 \end{matrix}$, or $(O)_a$—$\begin{matrix} R_5 \\ | \\ (C)_b \\ | \\ R_6 \end{matrix}$—$O\!\!\!-\!\!\!]_p$—

$R_1$ and $R_2$ each independently is a polymerizable unsaturated moiety having from 2 to 13 carbon atoms, $R_3$, $R_4$, $R_5$, and $R_6$ each independently is hydrogen, halogen, alkyl of from 1 to 10 carbon atoms or halogenated alkyl of from 1 to 10 carbon atoms, $R_9$, $R_{10}$, $R_{11}$, $R_{12}$, $R_{13}$ and $R_{14}$ each independently is hydrogen, alkyl having from 1 to 10 carbon atoms or aryl having from 6 to 10 carbon atoms, $Z_1$ and $Z_2$ each independently is a moiety including an acid group or a reactive acid derivative, a ,m and n each independently is 0 or 1, b, and p each independently is an integer from 1 to 10.

62. The composition of claim 57 wherein said solvent comprises ethanol.

63. The composition of claim 57 wherein said solvent comprises acetone.

64. The composition of claim 57 in a composition further comprises glass particles.

65. A polymerizable dental self-priming metal bonding composition, said composition, comprising:

a polymerizable aryl compound having at least one carboxylic acid group and at least one polymerizable group, and a phosphorous containing polymerizable compound having at least one polymerizable group and at least 20 percent by weight filler particles.

66. The composition of claim 65 wherein said filler is at least 40 percent by weight of said composition.

67. A dental method, comprising: providing a composition comprising an amount of volatile organic solvent effective to form a solution, at least 15 percent by weight of one or more polymerizable acrylate compounds and an effective amount of a photoinitiator, at least a portion of said polymerizable compounds being multifunctional polymerizable compounds having at least three acrylate moieties and a phosphate moiety, and a portion of said polymerizable compounds being aryl compounds, said polymerizable compounds being substantially soluble in said solvent, polymerizing said polymerizable composition to form a polymeric material which adheres to metal and metal alloy comprising at least 15 percent by weight of at least one metal selected from a group consisting of Au, Pt, Pd and Ag with a bond strength of at least 10 MPa.

68. The method of claim 67 wherein said composition comprises at least 2 percent by weight of said multifunctional polymerizable compounds, said bond strength is at least 20.

69. The method of claim 67 wherein said composition comprises at least 5 percent by weight of said multifunctional polymerizable compounds.

70. The method of claim 67 wherein said composition comprises at least 7 percent by weight of said multifunctional polymerizable compounds.

71. The method of claim 67 wherein at least a portion of said multifunctional compounds have a chemical structure within the scope of the general formula:

$(R')_n—Z'—(A')_m$ wherein each R' independently is an acrylate containing moiety, Z' is an organic moiety, each A' independently is an acid or acid ester, n is an integer greater than 2, m is an integer of 1 or more.

72. The method of claim 67 further comprising carboxylic acids.

73. A method for treating dental metal, comprising:

providing a first portion of a liquid composition for applying to a dental metal surface, said liquid composition comprising an amount of volatile organic solvent effective to form a solution, at least 15 percent by weight of one or more polymerizable acrylate compounds and an effective amount of a photoinitiator, at least a portion of said polymerizable compounds are multifunctional polymerizable compounds having at least three acrylate moieties and a phosphate moiety, a portion of said polymerizable compounds being aryl compounds, said polymerizable compound being substantially soluble in said solvent, polymerizing said composition to form a polymeric material which adheres to metal with a bond strength of at least 10 MPa when cured to form a primed metal surface.

74. The method of claim 73 further comprising a second portion of said liquid composition applied to said primed metal surface, said polymerizable compound in said second portion of said liquid priming adhesive composition being adapted to be cured to form a conditioned metal surface.

75. The method of claim 74 further comprising a polymerizable restorative composition applied to said conditioned metal surface.

76. The method of claim 75 wherein said polymerizable restorative composition is cured forming a polymeric restorative bonded to said metal with a bond strength at least 20 MPa.

77. The method of claim 74 wherein at least a portion of said multifunctional compounds have a chemical structure within the scope of the general formula:

$(R')_nZ'—(A')_m$ wherein each R' independently is an acrylate containing moiety, Z' is an organic moiety, each A' independently is an acid or acid ester, n is an integer greater than 2, m is an integer of 1 or more.

78. A dental method, comprising: providing a composition comprising amount of volatile organic solvent effective to form a solution, at least 15 percent by weight of one or more polymerizable acrylate compounds and an effective amount of a photoinitiator, at least a portion of said polymerizable compounds are multifunctional polymerizable compounds having at least three acrylate moieties and a phosphate moiety, and a portion of said polymerizable compounds are aryl compounds, polymerizing said polymerizable compounds being substantially soluble in said solvent, said polymerizable composition to form a polymeric material which adheres to metal with a bond strength of at least 10 Mpa.

79. The method of claim 78 wherein at least a portion of said polymerizable compounds are polymerizable compounds having at least one acid moiety and said polymerizable compounds having at least one acid moiety comprise at least 2 percent by weight of said composition.

80. The method of claim 78 wherein said composition further comprises at least 40 percent by weight filler.

* * * * *